United States Patent
Anderson et al.

(10) Patent No.: US 10,000,489 B2
(45) Date of Patent: Jun. 19, 2018

(54) COMPOUNDS $\alpha_v\beta_6$ INTEGRIN ANTAGONISTS

(71) Applicant: GlaxoSmithKline Intellectual Property Development Limited, Brentford, Middlesex (GB)

(72) Inventors: Niall Andrew Anderson, Stevenage (GB); Matthew Howard James Campbell-Crawford, Stevenage (GB); Ashley Paul Hancock, Stevenage (GB); John Martin Pritchard, Stevenage (GB); Joanna Mary Redmond, Stevenage (GB)

(73) Assignee: GlaxoSmithKline Intellectual Property Development Limited, Brentford, Middlesex (GB)

( * ) Notice: Subject to any disclaimer, the term of this patent is extended or adjusted under 35 U.S.C. 154(b) by 0 days. days.

(21) Appl. No.: 15/514,407

(22) PCT Filed: Sep. 22, 2015

(86) PCT No.: PCT/EP2015/071777
§ 371 (c)(1),
(2) Date: Mar. 24, 2017

(87) PCT Pub. No.: WO2016/046226
PCT Pub. Date: Mar. 31, 2016

(65) Prior Publication Data
US 2017/0298063 A1    Oct. 19, 2017

(30) Foreign Application Priority Data

Sep. 26, 2014  (GB) .................................. 1417011.2

(51) Int. Cl.
*C07D 471/04*   (2006.01)

(52) U.S. Cl.
CPC .................. *C07D 471/04* (2013.01)

(58) Field of Classification Search
CPC .................................................. C07D 471/04
See application file for complete search history.

(56) References Cited

U.S. PATENT DOCUMENTS

2004/0092454 A1   5/2004   Schadt et al.

FOREIGN PATENT DOCUMENTS

| WO | WO 99/30709 A1 | 6/1999 |
|---|---|---|
| WO | WO 99/31061 A1 | 6/1999 |
| WO | WO 00/72801 A2 | 12/2000 |
| WO | WO 00/78317 A1 | 12/2000 |
| WO | WO 01/24797 A1 | 4/2001 |
| WO | WO 01/34602 A2 | 5/2001 |
| WO | WO 01/096334 A2 | 12/2001 |
| WO | WO 02/07730 A1 | 1/2002 |
| WO | WO 02/22616 A2 | 3/2002 |
| WO | WO 02/053099 A2 | 7/2002 |
| WO | WO2004/058254 A1 | 7/2004 |
| WO | WO 2004/092454 A2 | 10/2004 |
| WO | WO 2005/082889 A1 | 9/2005 |
| WO | WO 2008/118455 A1 | 10/2008 |
| WO | WO 2009/055418 A1 | 4/2009 |
| WO | WO 2011/111880 A1 | 9/2011 |
| WO | WO 2014/154725 A1 | 10/2014 |
| WO | WO 2015/048819 A1 | 4/2015 |
| WO | WO 2016/046225 A1 | 3/2016 |
| WO | WO 2016/046230 A1 | 3/2016 |
| WO | WO 2016/046241 A1 | 3/2016 |
| WO | WO 2016/134223 A2 | 8/2016 |
| WO | WO 2016/145258 A1 | 9/2016 |
| WO | WO 2017/158072 A1 | 9/2017 |
| WO | WO 2017/162570 A1 | 9/2017 |
| WO | WO 2017/162572 A1 | 9/2017 |

OTHER PUBLICATIONS

International Search Report for International Application No. PCT/EP2015/071776, Nov. 5, 2015 (date of completion of the international search).
International Search Report for International Application No. PCT/EP2015/071777, Nov. 20, 2015 (date of completion of the international search).
International Search Report for International Application No. PCT/EP2015/071798, Nov. 4, 2015 (date of completion of the international search).
International Search Report for International Application No. PCT/EP2015/071782, Oct. 21, 2015 (date of completion of the international search).
Cho, et al., "Pirfenidone: an anti-fibrotic and cytoprotective agent as therapy for progressive kidney disease", *Expert Opin. Investig. Drugs*, vol. 19, No. 2, pp. 275-283 (2010).
Goodman et al., "Integrins as therapeutic targets", *Trends in Pharmacological Sciences*, vol. 33, No. 7, pp. 405-412 (2012).
Hahm et al., "avB6 integrin Regulates Renal Fibrosis and Inflammation in Alport Mouse", *The American Journal of Pathology*, vol. 170, No. 1, pp. 110-125 (2007).
Horan et al., "Partial Inhibition of Integrin avB6 Prevents Pulmonary Fibrosis without Exacerbating Inflammation", *Am. J. Respir. Crit. Care Med.*, vol. 177, pp. 56-65 (2008).

(Continued)

Primary Examiner — Laura L. Stockton
(74) Attorney, Agent, or Firm — Jane F. Djung; Kathryn A. Lutomski

(57) ABSTRACT

A compound of formula (I):

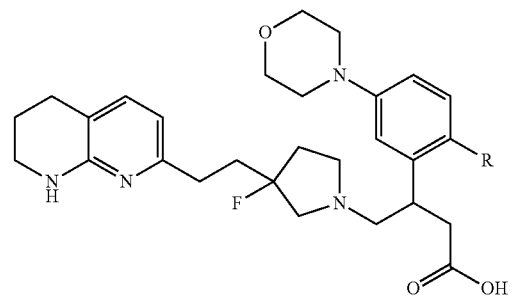

(I)

wherein R is H or F; or a salt thereof.

17 Claims, 1 Drawing Sheet

(56) References Cited

OTHER PUBLICATIONS

Margadant, C. et al., "Integrin-TGF-β crosstalk in fibrosis, cancer, and wound healing", *EMBO Reports*, vol. 11, No. 2, pp. 97-105 (2010).
Popov et al, "Integrin avB6 is a marker of the progression of biliary and portal liver fibrosis and a novel target for antifibrotic therapies", *Journal of Hepatology*, vol. 48 pp. 453-464 (2008).
Trevillian et al., "$\alpha_v\beta_6$ integrin expression in diseased and transplanted kidneys", *Kidney International*, vol. 66, pp. 1423-1433 (2004).
Whitman et al., "Nonpeptide αvβ3 antagonists. Part 9: Improved pharmacokinetic profile through the use of an aliphatic, des-amide backbone", *Bioorganic & Medicinal Chemistry Letters*, vol. 14, No. 17, pp. 4411-4415 (2004).
Woodcock, et al. The treatment of idiopathic pulmonary fibrosis,*F1000Prime Reports*, vol. 6, No. 16, pp. 1-9 (2014).
International Search Report for International Application No. PCT/EP2014/056013, dated May 9, 2014, 4 pages.
International Search Report for International Application No. PCT/EP2015/071776, dated Nov. 23, 2015, 4 pages.
International Search Report for International Application No. PCT/EP2015/071777, dated Nov. 26, 2015, 4 pages.
International Search Report for International Application No. PCT/EP2015/071782, dated Nov. 2, 2015, 4 pages.
International Search Report for International application No. PCT/EP2015/071798, dated Nov. 10, 2015, 4 pages.
International Search Report for International application No. PCT/EP2017/056204, dated May 15, 2017, 5 pages.
International Search Report for International application No. PCT/EP2017/056525, dated May 2, 2017, 4 pages.
International Search Report for International application No. PCT/EP2017/056527, dated May 2, 2017, 5 pages.
Restriction Requirement for U.S. Appl. No. 14/778,095, USPTO, dated Sep. 21, 2016, 9 pages.
Non-Final Office Action for U.S. Appl. No. 14/778,095, USPTO, dated Mar. 29, 2017, 14 pages.
Notice of Allowance for U.S. Appl. No. 14/778,095, USPTO, dated Nov. 3, 2017, 11 pages.
Notice of Allowance for U.S. Appl. No. 15/514,414, USPTO, dated Nov. 9, 2017, 19 pages.
Restriction Requirement for U.S. Appl. No. 15/514,416, USPTO, dated Aug. 14, 2017, 12 pages.
Non-Final Office Action for U.S. Appl. No. 15/514,416, USPTO, dated Nov. 2, 2017, 18 pages.
Notice of Allowance for U.S. Appl. No. 15/514,399, USPTO, dated Dec. 15, 2017, 13 pages.
Notice of Allowance for U.S. Appl. No. 15/514,399, USPTO, dated Aug. 21, 2017, 11 pages.

Figure 1. The X-ray crystal structure of compound (XVIII)
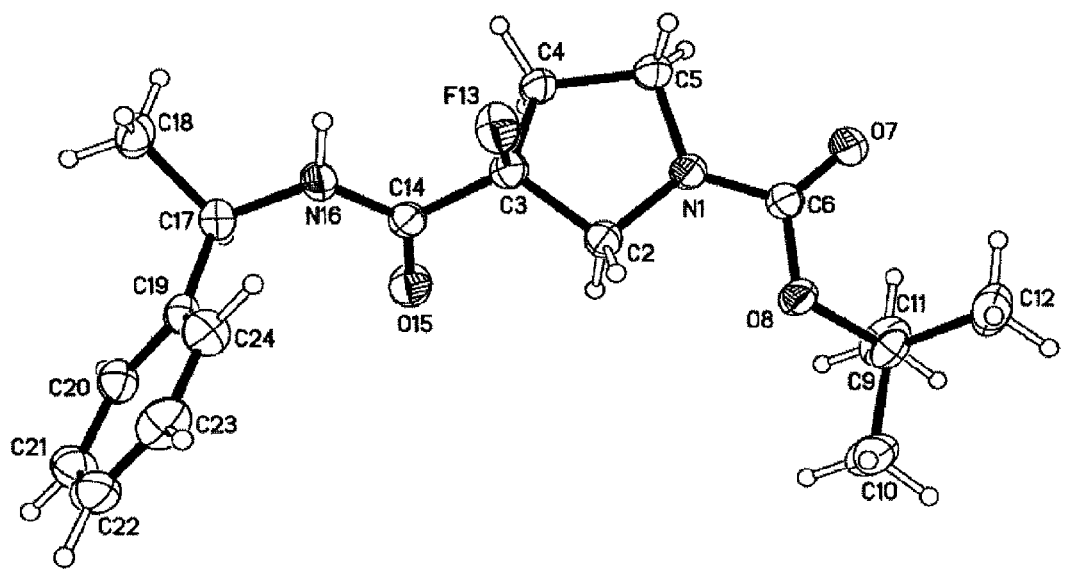
Figure 2. The X-ray crystal structure of compound XXIII
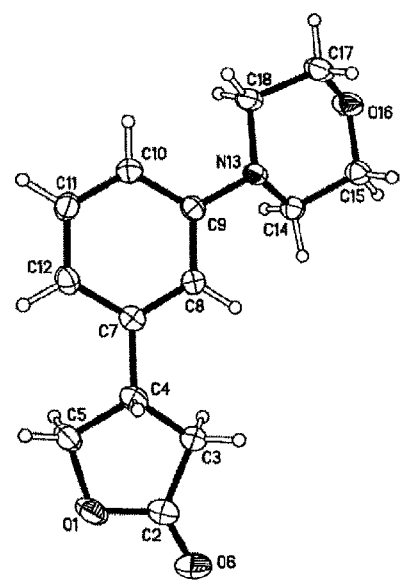

COMPOUNDS $\alpha_v\beta_6$ INTEGRIN ANTAGONISTS

This application is a § 371 of International Application No. PCT/EP2015/071777, filed Sep. 22, 2015, which claims the priority of GB 1417011.2, filed Sep. 26, 2014.

FIELD OF THE INVENTION

The present invention relates to pyrrolidine compounds being $\alpha_v\beta_6$ integrin antagonists, pharmaceutical compositions comprising such compounds and to their use in therapy, especially in the treatment of conditions for which an $\alpha_v\beta_6$ integrin antagonist is indicated, for the use of a compound in the manufacture of a medicament for the treatment of conditions in which an antagonist of $\alpha_v\beta_6$ integrin is indicated and a method for the treatment or prophylaxis of disorders in which antagonism of $\alpha_v\beta_6$ integrin is indicated in a human.

BACKGROUND OF THE INVENTION

Integrin superfamily proteins are heterodimeric cell surface receptors, composed of an alpha and beta subunit. At least 18 alpha and 8 beta subunits have been reported, which have been demonstrated to form 24 distinct alpha/beta heterodimers. Each chain comprises a large extracellular domain (>640 amino acids for the beta subunit, >940 amino acids for the alpha subunit), with a transmembrane spanning region of around 20 amino acids per chain, and generally a short cytoplasmic tail of 30-50 amino acids per chain. Different integrins have been shown to participate in a plethora of cellular biologies, including cell adhesion to the extracellular matrix, cell-cell interactions, and effects on cell migration, proliferation, differentiation and survival (Barczyk et al, *Cell and Tissue Research*, 2010, 339, 269).

Integrin receptors interact with binding proteins via short protein-protein binding interfaces. The integrin family can be grouped into sub-families that share similar binding recognition motifs in such ligands. A major subfamily is the RGD-integrins, which recognise ligands that contain an RGD (arginine-glycine-aspartic acid) motif within their protein sequence. There are 8 integrins in this sub-family, namely $\alpha_v\beta_1$, $\alpha_v\beta_3$, $\alpha_v\beta_5$, $\alpha_v\beta_6$, $\alpha_v\beta_8$, $\alpha_{IIb}\beta_3$, $\alpha_5\beta_1$, $\alpha_8\beta_1$, where nomenclature demonstrates that $\alpha_v\beta_1$, $\alpha_v\beta_3$, $\alpha_v\beta_5$, $\alpha_v\beta_6$, & $\alpha_v\beta_8$ share a common $\alpha_v$ subunit with a divergent $\beta_1$ subunit, and $\alpha_v\beta_1$, $\alpha_5\beta_1$ & $\alpha_8\beta_1$ share a common $\beta_1$ subunit with a divergent a subunit. The $\beta_1$ subunit has been shown to pair with 11 different α subunits, of which only the 3 listed above commonly recognise the RGD peptide motif (Humphries et al, *Journal of Cell Science*, 2006, 119, 3901).

The 8 RGD-binding integrins have different binding affinities and specificities for different RGD-containing ligands. Ligands include proteins such as fibronectin, vitronectin, osteopontin, and the latency associated peptides (LAPs) of Transforming Growth Factor $\beta_1$ and $\beta_3$ (TGF$\beta_1$ and TGF$\beta_3$). Integrin binding to the LAPs of TGF$\beta_1$ and TGF$\beta_3$ has been shown in several systems to enable activation of the TGF$\beta_1$ and TGF$\beta_3$ biological activities, and subsequent TGF$\beta$-driven biologies (Worthington et al, *Trends in Biochemical Sciences*, 2011, 36, 47). The diversity of such ligands, coupled with expression patterns of RGD-binding integrins, generates multiple opportunities for disease intervention. Such diseases include fibrotic diseases (Margadant et al, EMBO reports, 2010, 11, 97), inflammatory disorders, cancer (Desgrosellier et al, *Nature Reviews Cancer*, 2010, 10, 9), restenosis, and other diseases with an angiogenic component (Weis et al, *Cold Spring. Harb. Perspect Med.* 2011, 1, a 006478).

A significant number of $\alpha_v$ integrin antagonists (Goodman et al, *Trends in Pharmacological Sciences*, 2012, 33, 405) have been disclosed in the literature including inhibitory antibodies, peptides and small molecules. For antibodies these include the pan-$\alpha_v$ antagonists Intetumumab and Abituzumab (Gras, *Drugs of the Future*, 2015, 40, 97), the selective $\alpha_v\beta_3$ antagonist Etaracizumab, and the selective $\alpha_v\beta_6$ antagonist STX-100. Cilengitide is a cyclic peptide antagonist that inhibits both $\alpha_v\beta_3$ and $\alpha_v\beta_5$ and SB-267268 is an example of a compound (Wilkinson-Berka et al, *Invest. Ophthalmol. Vis. Sci,* 2006, 47, 1600), that inhibits both $\alpha_v\beta_3$ and $\alpha_v\beta_5$. Invention of compounds to act as antagonists of differing combinations of $\alpha_v$ integrins enables novel agents to be generated tailored for specific disease indications.

Pulmonary fibrosis represents the end stage of several interstitial lung diseases, including the idiopathic interstitial pneumonias, and is characterised by the excessive deposition of extracellular matrix within the pulmonary interstitium. Among the idiopathic interstitial pneumonias, idiopathic pulmonary fibrosis (IPF) represents the commonest and most fatal condition with a typical survival of 3 to 5 years following diagnosis. Fibrosis in IPF is generally progressive, refractory to current pharmacological intervention and inexorably leads to respiratory failure due to obliteration of functional alveolar units. IPF affects approximately 500,000 people in the USA and Europe.

There are in vitro experimental, animal and IPF patient immunohistochemistry data to support a key role for the epithelially restricted integrin, $\alpha_v\beta_6$, in the activation of TGF$\beta$1. Expression of this integrin is low in normal epithelial tissues and is significantly up-regulated in injured and inflamed epithelia including the activated epithelium in IPF. Targeting this integrin, therefore, reduces the theoretical possibility of interfering with wider TGF$\beta$ homeostatic roles. Partial inhibition of the $\alpha_v\beta_6$ integrin by antibody blockade has been shown to prevent pulmonary fibrosis without exacerbating inflammation (Horan G S et al Partial inhibition of integrin $\alpha_v\beta_6$ prevents pulmonary fibrosis without exacerbating inflammation. *Am J Respir Crit Care Med* 2008 177 56-65). Outside of pulmonary fibrosis, $\alpha_v\beta_6$ is also considered an important promoter of fibrotic disease of other organs, including liver and kidney (Reviewed in Henderson N C et al Integrin-mediated regulation of TGF$\beta$ in Fibrosis, Biochimica et Biophysica Acta—Molecular Basis of Disease 2013 1832.891-896), suggesting that an $\alpha_v\beta_6$ antagonist could be effective in treating fibrotic diseases in multiple organs.

Consistent with the observation that several RGD-binding integrins can bind to, and activate, TGF$\beta$, different $\alpha_v$ integrins have recently been implicated in fibrotic disease (Henderson N C et al Targeting of $\alpha_v$ integrin identifies a core molecular pathway that regulates fibrosis in several organs *Nature Medicine* 2013 Vol 19, Number 12: 1617-1627; Sarrazy V et al Integrins αvβ5 and αvβ3 promote latent TGF-β1 activation by human cardiac fibroblast contraction *Cardiovasc Res* 2014 102:407-417; Minagawa S et al Selective targeting of TGF-β activation to treat fibroinflammatory airway disease *Sci Transl Med* 2014 Vol 6, Issue 241: 1-14; Reed N I et al. The $\alpha_v\beta_1$ integrin plays a critical in vivo role in tissue fibrosis *Sci Transl Med* 2015 Vol 7, Issue 288: 1-8). Therefore inhibitors against specific members of the RGD binding integrin families, or with specific selectivity fingerprints within the RGD binding integrin family, may be effective in treating fibrotic diseases in multiple organs.

SAR relationships of a series of integrin antagonists against $\alpha_v\beta_3$, $\alpha_v\beta_5$, $\alpha_v\beta_6$ and $\alpha_v\beta_8$ have been described (Macdonald, S J F et al. Structure activity relationships of ac integrin antagonists for pulmonary fibrosis by variation in aryl substituents. *ACS Med Chem Lett* 2014, 5, 1207-1212. 19 Sep. 2014).

It is desirable to provide $\alpha_v\beta_6$ antagonists which may also have activities against other $\alpha_v$ integrins, such as $\alpha_v\beta_1$, $\alpha_v\beta_5$ or $\alpha_v\beta_8$.

BRIEF SUMMARY OF THE INVENTION

In a first aspect of the present invention, there is provided a compound of formula (I) or a salt thereof more particularly a compound of formula (I) or a pharmaceutically acceptable salt thereof:

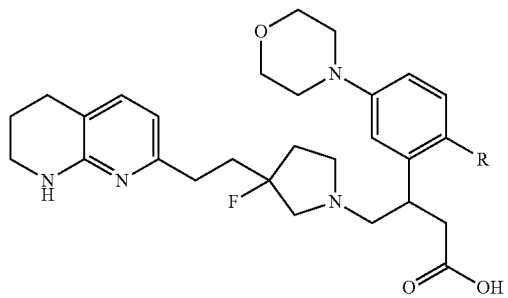

wherein R represents H or F.

Compounds of formula (I) and their salts have $\alpha_v\beta_6$ antagonist activity and are believed to be of potential use for the treatment or prophylaxis of certain disorders. The term $\alpha_v\beta_6$ antagonist activity includes $\alpha_v\beta_6$ inhibitor activity herein.

In a second aspect of the present invention, there is provided a pharmaceutical composition comprising a compound of formula (I) or a pharmaceutically acceptable salt thereof and one or more pharmaceutically acceptable carriers, diluents or excipients.

In a third aspect of the present invention, there is provided a compound of formula (I), or a pharmaceutically acceptable salt thereof for use in therapy, in particular in the treatment of a disease or condition for which an $\alpha_v\beta_6$ integrin receptor antagonist is indicated.

In a fourth aspect of the present invention, there is provided a method of treatment or prophylaxis of a disease or condition for which an $\alpha_v\beta_6$ integrin receptor antagonist is indicated in a human in need thereof which comprises administering to a human in need thereof a therapeutically effective amount of compound of formula (I) or a pharmaceutically acceptable salt thereof.

In a fifth aspect of the present invention, there is provided the use of a compound of formula (I), or a pharmaceutically acceptable salt thereof in the manufacture of a medicament for the treatment of a disease or condition for which an $\alpha_v\beta_6$ integrin receptor antagonist is indicated.

DETAILED DESCRIPTION OF THE INVENTION

In a first aspect of the invention there is provided a compound of formula (I) or a salt thereof:

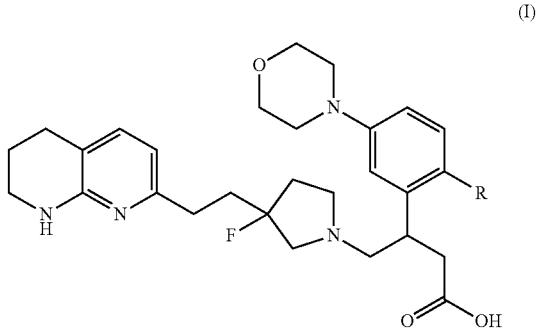

wherein R represents H or F.

One compound of Formula (I) is 4-(3-fluoro-3-(2-(5, 6, 7, 8-tetrahydro-1, 8-naphthyridin-2-yl) ethyl) pyrrolidin-1-yl)-3-(3-morpholinophenyl) butanoic acid (IA) or a salt thereof:

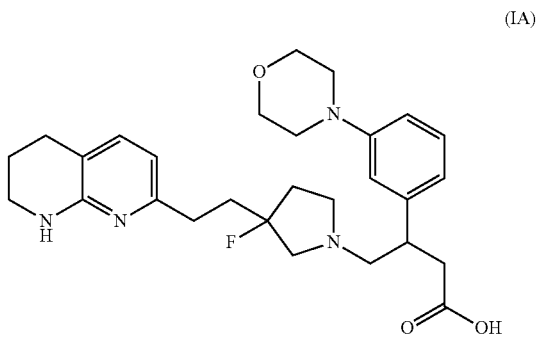 [SMILES: O=C(O)CC(CN1CCC(F)(CCc2ccc3c(n2)NCCC3)C1)c1cccc(N2CCOCC2)c1]

In one embodiment the compound of formula (IA) is a pharmaceutically acceptable salt of 4-(3-fluoro-3-(2-(5, 6, 7, 8-tetrahydro-1, 8-naphthyridin-2-yl) ethyl) pyrrolidin-1-yl)-3-(3-morpholinophenyl) butanoic acid.

In an embodiment the compound of formula (IA) has the formula (IA1):

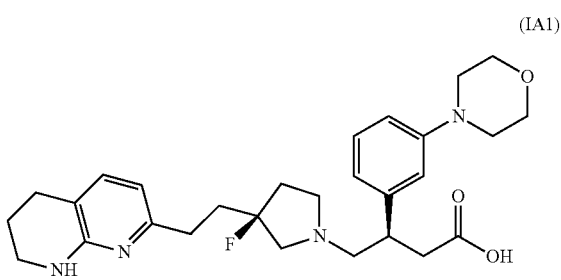 [SMILES: O=C(O)C[C@@H](CN1CC[C@@](F)(CCc2ccc3c(n2)NCCC3)C1)c1cccc(N2CCOCC2)c1]

(R)-4-((S)-3-fluoro-3-(2-(5, 6, 7, 8-tetrahydro-1, 8-naphthyridin-2-yl) ethyl) pyrrolidin-1-yl)-3-(3-morpholinophenyl) butanoic acid, or a pharmaceutically acceptable salt thereof.

In another embodiment the compound of formula (I) has the formula (IA2):

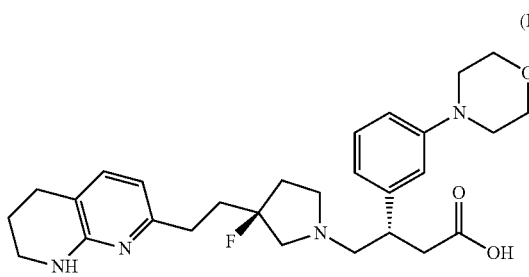

(IA2)

(S)-4-((S)-3-fluoro-3-(2-(5, 6, 7, 8-tetrahydro-1, 8-naphthyridin-2-yl) ethyl) pyrrolidin-1-yl)-3-(3-morpholinophenyl) butanoic acid, or a pharmaceutically acceptable salt thereof.

In another embodiment the compound of formula (I) has the formula (IA3):

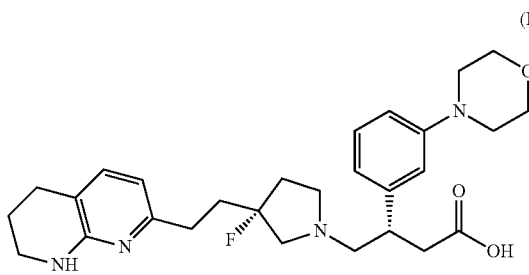

(IA3)

(S)-4-((R)-3-fluoro-3-(2-(5, 6, 7, 8-tetrahydro-1, 8-naphthyridin-2-yl) ethyl) pyrrolidin-1-yl)-3-(3-morpholinophenyl) butanoic acid, or a pharmaceutically acceptable salt thereof.

In another embodiment the compound of formula (I) has the formula (IA4):

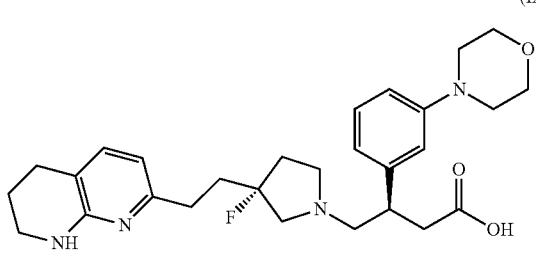

(IA4)

(R)-4-((R)-3-fluoro-3-(2-(5, 6, 7, 8-tetrahydro-1, 8-naphthyridin-2-yl) ethyl) pyrrolidin-1-yl)-3-(3-morpholinophenyl) butanoic acid, or a pharmaceutically acceptable salt thereof.

Another compound of Formula (I) is 4-(3-fluoro-3-(2-(5, 6, 7, 8-tetrahydro-1, 8-naphthyridin-2-yl) ethyl) pyrrolidin-1-yl)-3-(2-fluoro-5-morpholinophenyl) butanoic acid (IB) or a salt thereof:

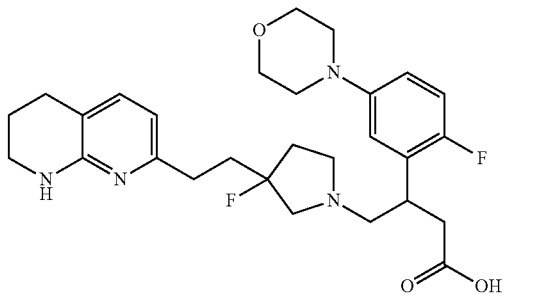

(IB)

In one embodiment the compound of formula (IB) is a pharmaceutically acceptable salt of 4-(3-fluoro-3-(2-(5, 6, 7, 8-tetrahydro-1, 8-naphthyridin-2-yl) ethyl) pyrrolidin-1-yl)-3-(2-fluoro-5-morpholinophenyl) butanoic acid.

In an embodiment the compound of formula (IB) has the formula of (IB1):

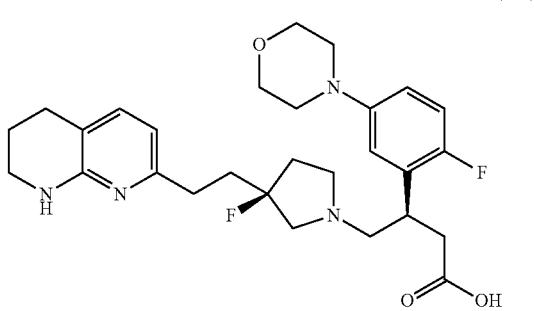

(IB1)

(R)-4-((S)-3-fluoro-3-(2-(5, 6, 7, 8-tetrahydro-1, 8-naphthyridin-2-yl) ethyl) pyrrolidin-1-yl)-3-(2-fluoro-5-morpholinophenyl) butanoic acid, or a pharmaceutically acceptable salt thereof.

In another embodiment the compound of formula (IB) has the formula of (IB2):

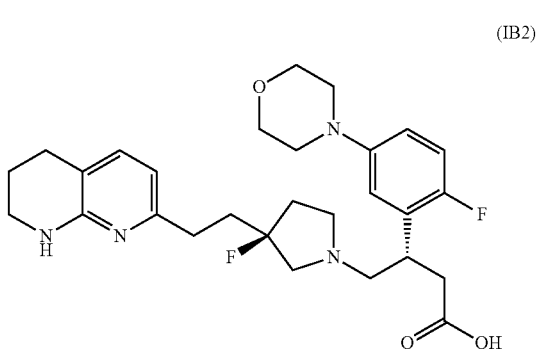 [SMILES: O=C(O)C[C@H](CN1CC[C@@](F)(CCc2ccc3c(n2)NCCC3)C1)c1cc(N2CCOCC2)ccc1F]

(IB2)

(S)-4-((S)-3-fluoro-3-(2-(5, 6, 7, 8-tetrahydro-1, 8-naphthyridin-2-yl) ethyl) pyrrolidin-1-yl)-3-(2-fluoro-5-morpholinophenyl) butanoic acid, or a pharmaceutically acceptable salt thereof.

In another embodiment the compound of formula (IB) has the formula of (IB3):

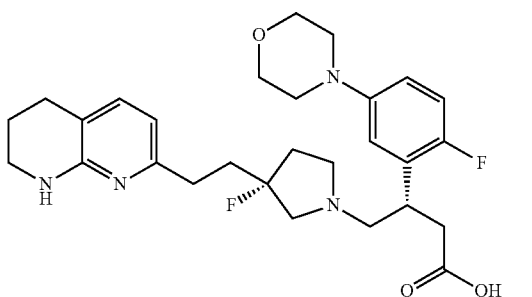

(S)-4-((R)-3-fluoro-3-(2-(5, 6, 7, 8-tetrahydro-1, 8-naphthyridin-2-yl) ethyl) pyrrolidin-1-yl)-3-(2-fluoro-5-morpholinophenyl) butanoic acid, or a pharmaceutically acceptable salt thereof.

In another embodiment the compound of formula (IB) has the formula of (IB4):

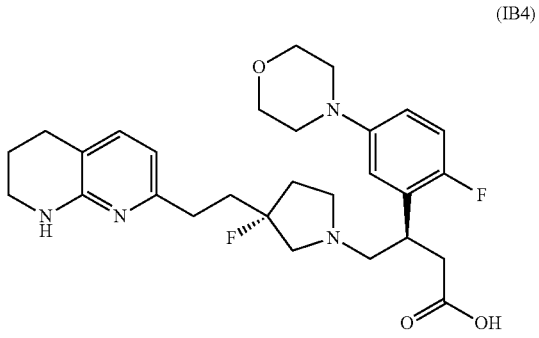 [SMILES: O=C(O)C[C@@H](CN1CC[C@](F)(CCc2ccc3c(n2)NCCC3)C1)c1cc(N2CCOCC2)ccc1F]

(R)-4-((R)-3-fluoro-3-(2-(5, 6, 7, 8-tetrahydro-1, 8-naphthyridin-2-yl) ethyl) pyrrolidin-1-yl)-3-(2-fluoro-5-morpholinophenyl) butanoic acid, or a pharmaceutically acceptable salt thereof.

Compounds of formula (I) have both a basic amine group and a carboxylic acid group and can consequently form an internal salt, i.e. a zwitterion or inner salts. Therefore in an embodiment the compound of formula (I) is 4-(3-fluoro-3-(2-(5, 6, 7, 8-tetrahydro-1, 8-naphthyridin-2-yl) ethyl) pyrrolidin-1-yl)-3-(3-morpholinophenyl) butanoic acid or 4-(3-fluoro-3-(2-(5,6,7,8-tetrahydro-1,8-naphthyridin-2-yl)ethyl) pyrrolidin-1-yl)-3-(2-fluoro-5-morpholinophenyl)butanoic acid or any one of compounds IA1, IA2, IA3, IA4, IB1, 182, IB3 or IB4 in a zwitterionic salt form. In another embodiment the compound of formula (I) is 4-(3-fluoro-3-(2-(5, 6, 7, 8-tetrahydro-1, 8-naphthyridin-2-yl)ethyl) pyrrolidin-1-yl)-3-(3-morpholinophenyl) butanoic acid or 4-(3-fluoro-3-(2-(5,6,7,8-tetrahydro-1,8-naphthyridin-2-yl)ethyl)pyrrolidin-1-yl)-3-(2-fluoro-5-morpholinophenyl)butanoic acid or any one of compounds IA1, IA2, IA3, IA4, IB1, IB2, IB3 or IB4 in a non-zwitterionic form.

It will be appreciated that the present invention covers compounds of formula (I) as the parent compound, as a zwitterion (the parent compound is protonated internally by its carboxylic acid group and normally exists as a zwitterion) and as salts thereof, for example as a pharmaceutically acceptable salt thereof. In one embodiment the invention relates to compounds of formula (I) or a pharmaceutically acceptable salt thereof.

For a review on suitable salts see Berge et al., *J. Pharm. Sci.*, 66:1-19, (1977). Suitable pharmaceutically acceptable salts are listed in P H Stahl and C G Wermuth, editors, *Handbook of Pharmaceutical Salts; Properties, Selection and Use*, Weinheim/Zurich: Wiley-VCH/VHCA, 2002. Suitable pharmaceutically acceptable salts can include acid addition salts with inorganic acids such, for example, as hydrochloric acid, hydrobromic acid, orthophosphoric acid, nitric acid, phosphoric acid, or sulphuric acid, or with organic acids such, for example as methanesulphonic acid, ethanesulphonic acid, p-toluenesulphonic acid, acetic acid, propionic acid, lactic acid, citric acid, fumaric acid, malic acid, succinic acid, salicylic acid, maleic acid, glycerophosphoric acid, tartaric, benzoic, glutamic, aspartic, benzenesulphonic, naphthalenesulphonic such as 2-naphthalenesulphonic, hexanoic acid or acetylsalicylic acid. Particularly suitable acids are fumaric and maleic acid. Typically, a pharmaceutically acceptable salt may readily be prepared by using a desired acid or base as appropriate. The resultant salt may precipitate from solution and be collected by filtration or may be recovered by evaporation of the solvent.

Other non-pharmaceutically acceptable salts, e.g. formates, oxalates or trifluoroacetates, may be used, for example in the isolation of the compounds of formula (I), and are included within the scope of this invention.

A pharmaceutically acceptable base addition salt can be formed by reaction of a compound of formula (I) with a suitable organic base, (e.g. triethylamine, ethanolamine, triethanolamine, choline, arginine, lysine or histidine), optionally in a suitable solvent, to give the base addition salt which is usually isolated, for example, by crystallisation and filtration. Pharmaceutically acceptable base salts include ammonium salts, alkali metal salts such as those of sodium and potassium, alkaline earth metal salts such as those of calcium and magnesium and salts with organic bases, including salts of primary, secondary and tertiary amines, such as isopropylamine, diethylamine, ethanolamine, trimethylamine, dicyclohexyl amine and N-methyl-D-glucamine.

The invention includes within its scope all possible stoichiometric and non-stoichiometric forms of the salts of the compounds of formula (I).

The compounds of formula (I) may be in crystalline or amorphous form. Furthermore, some of the crystalline forms of the compounds of formula (I) may exist as polymorphs, which are included within the scope of the present invention. Polymorphic forms of compounds of formula (I) may be characterized and differentiated using a number of conventional analytical techniques, including, but not limited to, X-ray powder diffraction (XRPD) patterns, infrared (IR) spectra, Raman spectra, differential scanning calorimetry (DSC), thermogravimetric analysis (TGA) and solid state nuclear magnetic resonance (SSNMR).

The compounds of formula (I) may also be prepared as an amorphous molecular dispersion in a polymer matrix, such as hydroxypropylmethyl cellulose acetate succinate, using a spray-dried dispersion (SDD) process to improve the stability and solubility of the drug substance.

It will be appreciated that many organic compounds can form complexes with solvents in which they are reacted or from which they are precipitated or crystallized. These complexes are known as "solvates". For example, a complex with water is known as a "hydrate". Solvents with high boiling points and/or capable of forming hydrogen bonds such as water, xylene, N-methyl pyrrolidinone, methanol and ethanol may be used to form solvates. Methods for identification of solvates include, but are not limited to, NMR and microanalysis. It will be appreciated that crystalline forms optionally may be solvated to form, for example, pharmaceutically acceptable solvates, such as hydrates which may be stoichiometric hydrates as well as compounds containing variable amounts of water. Solvates include stoichiometric solvates and non-stoichiometric solvates. Compounds of formula (I) may exist in solvated or non-solvated form.

The compounds described herein contain two asymmetric centres so that optical isomers, e.g. diastereoisomers and enantiomers may be formed. Accordingly, the present invention encompasses isomers of the compounds of formula (I) whether as individual isomers isolated such as to be substantially free of the other isomer (i.e. pure) or as mixtures. An individual isomer isolated such as to be substantially free of the other isomer (i.e. pure) may be isolated such that less than 10%, particularly less than about 1%, for example less than about 0.1% of the other isomer is present.

It will be understood by those skilled in the art that certain diastereoisomers may be less active than others and that the activity of an individual diastereoisomer may fall below a selected limit.

Separation of isomers may be achieved by conventional techniques known to those skilled in the art, e.g. by fractional crystallisation, chromatography, HPLC or a combination of these techniques.

Compounds of formula (I) may exist in one of several tautomeric forms. It will be understood that the present invention encompasses all tautomers of the compounds of formula (I) whether as individual tautomers or as mixtures thereof.

It will be appreciated from the foregoing that included within the scope of the invention are solvates, isomers and polymorphic forms of the compounds of formula (I) and salts thereof.

Compound Preparation

The compounds of the invention may be made by a variety of methods, including standard chemistry. Any previously defined variable will continue to have the previously defined meaning unless otherwise indicated. Illustrative general synthetic methods are set out below and then specific compounds of the invention are prepared in the working Examples.

It will be appreciated by those skilled in the art that the (E) or (Z) description of some intermediate compounds which can exist in two geometrical isomers, may contain the other geometric isomer as a minor component.

Compounds of structural formula (I) may be prepared by a process involving first deprotection of a compound of structural formula (II), i.e. cleavage of the ester group, followed optionally by conversion to a salt:

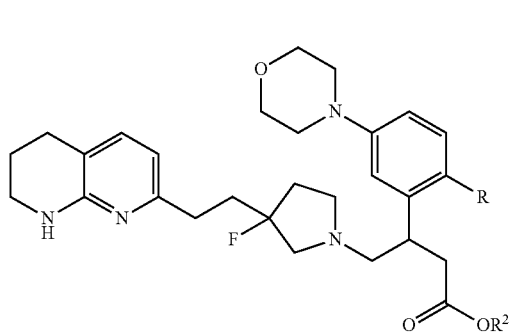

(II)

where $R^2$ is a $C_1$-$C_6$ alkyl group for example a tert-Bu, ethyl or methyl group. Alternatively $R^2$ is a chiral alcohol for example (−)-menthol [(1R,2S,5R)-2-isopropyl-5-methylcyclohexanol].

A sixth aspect of the invention provides a compound of formula (II).

The deprotection of compound of structural formula (II) where $R^2$ is methyl, ethyl, a chiral alcohol such as menthol or tert-Bu may be accomplished by acid hydrolysis using for example hydrochloric, hydrobromic, sulfuric, or trifluoroacetic acid, in an inert solvent, such as dichloromethane, 2-methyl-tetrahydrofuran, tetrahydrofuran, 1,4-dioxane or cyclopentyl methyl ether or water.

Alternatively the deprotection of compound of structural formula (II) where $R^2$ is methyl, ethyl or a chiral alcohol such as menthol may be accomplished by base hydrolysis using for example lithium hydroxide, sodium hydroxide, potassium hydroxide in a suitable solvent, e.g. an aqueous solvent such as aqueous methanol.

After the cleavage of the ester group the resulting product may be converted to the required salt by methods well known to those skilled in the art.

In one embodiment the conversion of the zwitterion to the fumarate salt is achieved by treatment of an ethanol solution of the zwitterion with an ethanol solution of fumaric acid, heating the resulting salt solution to 40° C. and allowing to cool to 5° C. for crystallisation to occur.

In another embodiment the conversion of the zwitterion to the maleate salt is achieved by treatment of an acetonitrile solution of the zwitterion with an aqueous solution of maleic acid, heating the resulting solution to 40° C. and allowing to cool to 5° C. for crystallisation to occur.

Compounds of structural formula (II) may be obtained from compounds of structural formula (III):

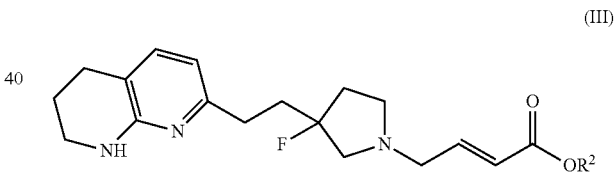

(III)

where $R^2$ is as defined above, by reaction with a boronic acid compound of structural formula (IV) where R is H or F:

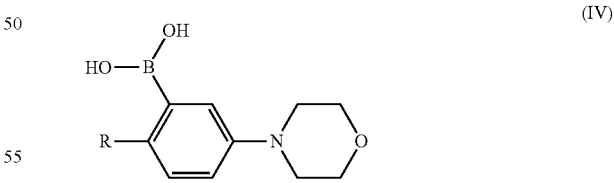

(IV)

Alternatively, a boronate ester, such as pinacol ester, may be used, which provides the parent boronic acid in situ. Compounds of structural formula (IV) are commercially available e.g. from Enamine LLC, Princeton Corporate Plaza, 7 Deer Park Drive Ste. 17-3, Monmouth Jct. N.J. (USA) 08852, Manchester Organics or Fluorochem. The reaction between the compound of structural formulae (III) and (IV) may be performed in the presence of a suitable catalyst, such as a rhodium catalyst, for example the dimer of rhodium (1,5-cyclooctadiene) chloride, [Rh(COD)Cl]$_2$ and an additive such as a phosphine ligand, for example bis(diphenylphosphino)-1,1'-binaphthyl (BINAP), preferably in the presence of a base, such as aqueous potassium hydroxide, at elevated temperature, such as 50-95° C., and in a water-miscible solvent, such as 1,4-dioxane. The reaction is preferably carried out under strictly anaerobic conditions, where the reaction mixture is purged with an inert gas such as nitrogen, and evacuated under reduced pressure, repeating this process of evacuation and purging with nitrogen three times. Alternatively the reaction may be carried out in a microwave vial and the mixture is heated in a microwave reactor at elevated temperature. This reaction produces a mixture of isomers, normally in the ratio of 1:1. The mixture of isomers produced can be separated by chromatography, HPLC or by crystallisation. An asymmetric synthesis can be achieved by the inclusion of one enantiomer of the chiral ligand, for example (R)-(+)-2, 2'-bis (diphenylphosphino)-1, 1'-binaphthyl (R-BINAP) in the presence of a catalyst based on a rhodium compound. The geometry of the double bond in the compound of structural formula (III) may be (E) or mixture of (E) and (Z) isomers, preferably pure (E) isomer.

The reaction between one enantiomer of a compound of formula (III) with a compound of formula (IV) produces two diastereoisomers, in approximately 1:1 ratio, which can be separated by crystallisation, chromatography, or by HPLC. Preferred method of separation is chiral HPLC on a chiral support, such as Chiralpak or Chiralcel columns. The ratio of the diastereoisomers formed can be increased substantially to for example approximately 80:20, or higher in the presence of about 10% of additives, such as (R)-(+)-2,2'-bis (diphenylphosphino)-1,1'-binaphthalene [(R)-BINAP], which provides as the major isomer the biologically more active diastereoisomer.

Alternatively, various combinations of compound (III) with different chiral R² groups, ligand, boronic acid (IV), catalyst and solvent selected by those skilled in the art or by screening large numbers of combinations may afford a higher ratio of diastereoisomers.

The diastereoisomeric ratio can be further increased to, for example, greater than 99:1, by chiral HPLC, or by crystallisation.

Compounds of structural formula (III) may be obtained from compounds of structural formula (V):

(V)

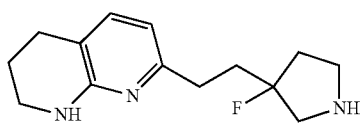

by reaction with a compound of structural formula (VI)

(VI)

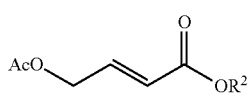

where R² is as defined above, in the presence of an organic base such as N,N-diisopropylethylamine ("DIPEA") and a suitable palladium-based catalyst, for example PdCl₂(dppf)-CH₂Cl₂ [1,1'-bis(diphenylphosphino) ferrocene]dichloropalladium(II), complex with dichloromethane, in a solvent such as dichloromethane. The compound of formula (V) can be used as the parent compound, or be generated in situ from a salt, such as the dihydrochloride salt, in the presence of a tertiary amine base.

Compounds of structural formula (VI) may be prepared by methods described herein. By way of illustration compound of structural formula (VI), where R² is methyl, and the double bond having the (E) geometry, can be prepared by the method shown below, starting from the commercially available methyl 4-bromocrotonate and sodium or potassium acetate in acetonitrile at elevated temperature e.g. 50° C.:

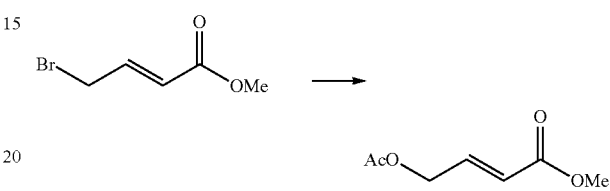

Compounds of structural formula (V) may be prepared from compounds of structural formula (VII):

(VII)

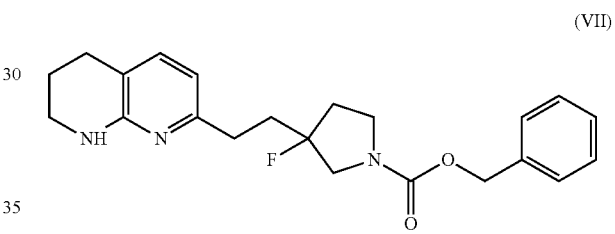

by catalytic hydrogenolysis for example using a palladium catalyst deposited on carbon, in an inert solvent, such as ethanol or ethyl acetate.

Compounds of structural formula (VII) may be obtained from compounds of structural formula (VIII):

(VIII)

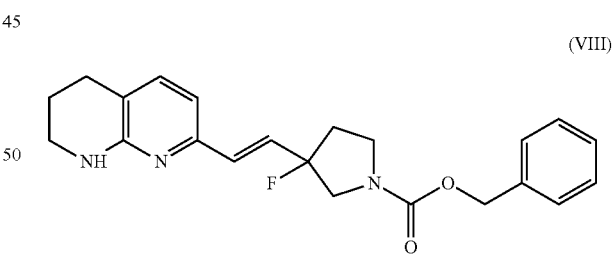

by diimide reduction, generated for example from benzenesulfonyl hydrazide in the presence of a base, such as potassium carbonate, in a suitable solvent, such as DMF, and at elevated temperature, such as 130° C.

Compounds of structural formula (VIII) exist as geometrical isomers e.g. (E) or (Z)-form and may be used either as pure isomers or as mixtures. Compounds of structural formula (VIII) may be obtained starting from known commercially available (e.g. from Wuxi App Tec, 288 Fute Zhong Road, Waigaoquiao Free Trade, Shanghai 200131, China) compounds of structural formula (IX):

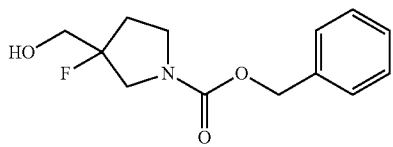

(IX)

which may be oxidised e.g. with sulphur trioxide in pyridine to the corresponding aldehyde of structural formula (X):

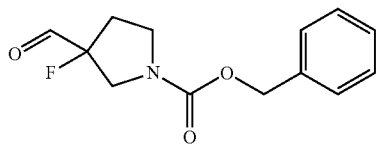

(X)

This compound of structural formula (X) may then be reacted, which may be without isolation of the compound of formula (X), with an ylide of structural formula (XI):

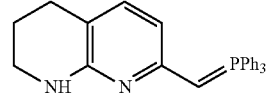

(XI)

to thereby form the compound of formula (VIII) which exists as a mixture of geometrical isomers (E) and (Z). It will be appreciated by those skilled in the art that there are other methods for forming compound of formula (VIII) from the aldehyde (X). The geometrical isomers can be separated by chromatography or used in the next step as a mixture. This overall scheme for preparation of compounds of structural formula (I) is summarised below as Scheme (I):

Scheme (I):

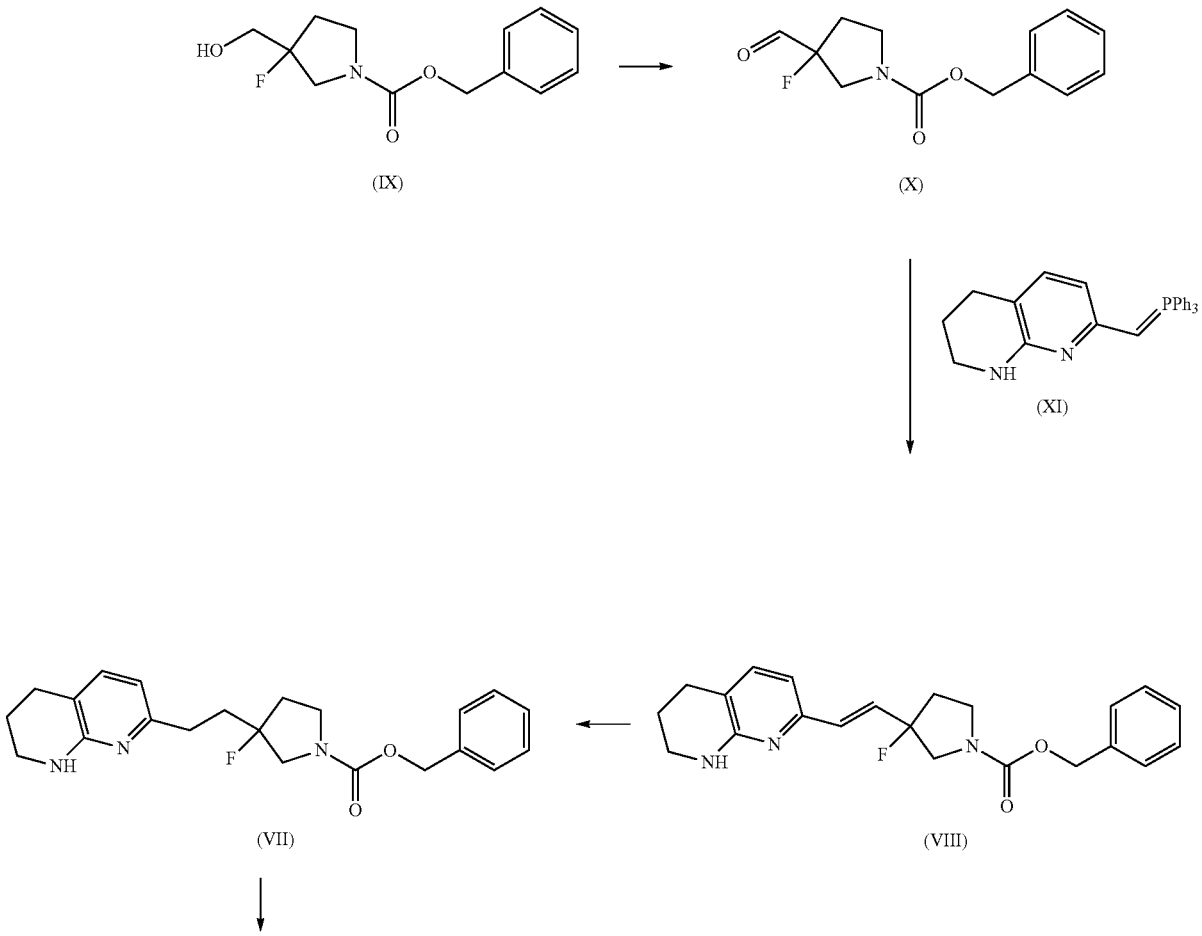

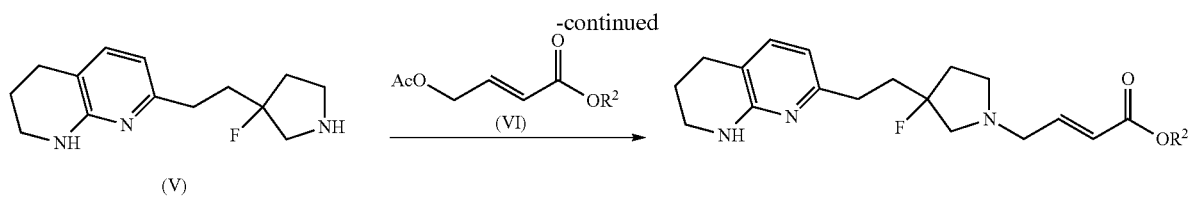

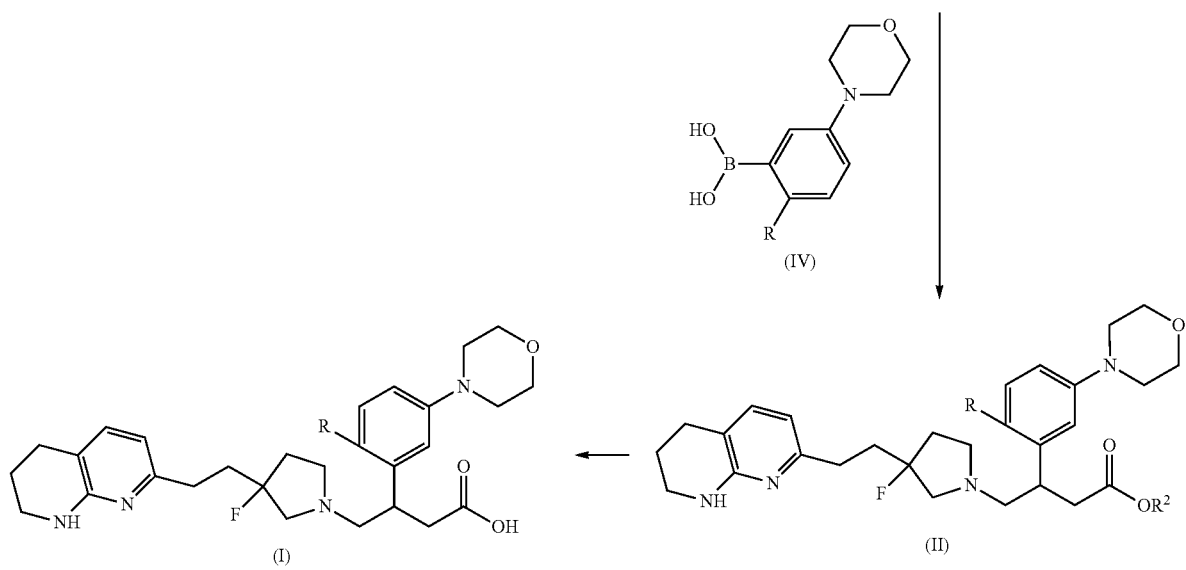

Ylides of structural formula (XI) may be made starting from compounds of formula (XII) (available from Fluorochem):

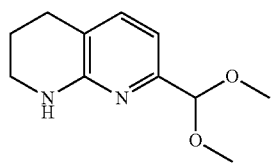
(XII)

which by reaction with first hydrochloric acid followed by neutralisation with sodium bicarbonate may then be converted into an aldehyde of structural formula (XIII):

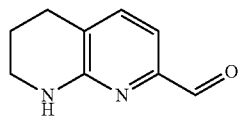
(XIII)

which may be reduced e.g. using sodium borohydride to the corresponding alcohol of structural formula (XIV):

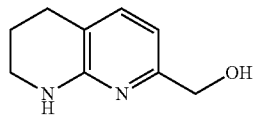
(XIV)

(See also the routes disclosed in US-A-20040092538 for preparation of alcohol of formula (XIV)) which may then be brominated e.g. using phosphorus tribromide to produce the corresponding bromo compound of structural formula (XV):

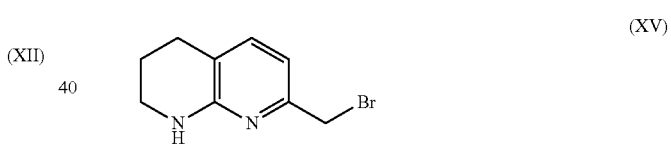
(XV)

which may be converted to the triphenylphosphonium bromide (XVI) by reacting with triphenylphosphine in a solvent such as acetonitrile.

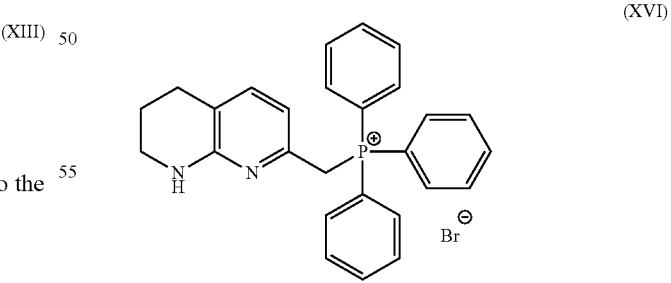
(XVI)

The abovementioned ylide compound of structural formula (XI) may be obtained by reaction of compound of structural formula (XVI) with a base, such as a solution of potassium tert-butoxide in an inert solvent, such as THF. The ylide of structural formula (XI) may be isolated or preferably formed in situ and reacted in the same vessel with an aldehyde of structural formula (X) without prior isolation.

The overall scheme for the preparation of ylide of structural formula (XI) is summarised below as Scheme (II):

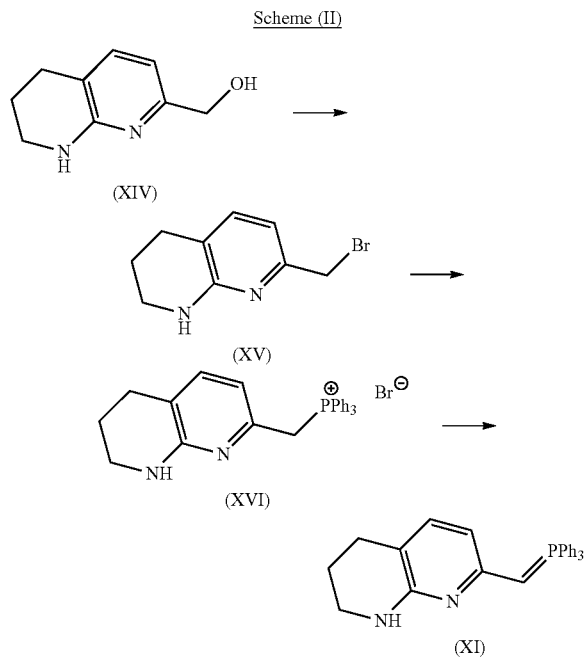

Each of the two commercially available enantiomers of compound of formula (IX) provides one diastereoisomer of compound of formula (I) which is more potent than the other.

It will be appreciated that in any of the routes described above it may be advantageous to protect one or more functional groups. Examples of protecting groups and the means for their removal can be found in T. W. Greene 'Protective Groups in Organic Synthesis' (3rd edition, J. Wiley and Sons, 1999). Suitable amine protecting groups include acyl (e.g. acetyl), carbamate (e.g. 2',2',2'-trichloroethoxycarbonyl, benzyloxycarbonyl or t-butoxycarbonyl) and arylalkyl (e.g. benzyl), which may be removed by hydrolysis (e.g. using an acid such as hydrochloric acid in dioxane or trifluoroacetic acid in dichloromethane) or reductively (e.g. hydrogenolysis of a benzyl or benzyloxycarbonyl group or reductive removal of a 2',2',2'-trichloroethoxycarbonyl group using zinc in acetic acid) as appropriate. Other suitable amine protecting groups include trifluoroacetyl (—COCF$_3$) which may be removed by base catalysed hydrolysis.

It will be appreciated that in any of the routes described above, the precise order of the synthetic steps by which the various groups and moieties are introduced into the molecule may be varied. It will be within the skill of the practitioner in the art to ensure that groups or moieties introduced at one stage of the process will not be affected by subsequent transformations and reactions, and to select the order of synthetic steps accordingly.

Certain compounds of formulae (III), (V) to (VIII), (X), (XI), (XV) and (XVI) are also believed to be novel and therefore form a yet further aspect of the invention.

The absolute configuration of compounds of formula (I) may be obtained following an independent enantioselective synthesis from an intermediate of known absolute configuration. Alternatively an enantiomerically pure compound of formula (I) may be converted into a compound whose absolute configuration is known. In either case comparison of spectroscopic data, optical rotation and retention times on an analytical HPLC column may be used to confirm absolute configuration. A third option where feasible is determination of absolute configuration through X-Ray crystallography.

Methods of Use

The compounds of formula (I) and salts thereof are believed to have $\alpha_v$ integrin antagonist activity, particularly $\alpha_v\beta_6$ receptor activity, and thus have potential utility in the treatment of diseases or conditions for which an $\alpha_v\beta_6$ antagonist is indicated.

The present invention thus provides a compound of formula (I) or a pharmaceutically acceptable salt thereof for use in therapy. The compound of formula (I) or pharmaceutically acceptable salt thereof can be for use in the treatment of a disease or condition for which an $\alpha_v\beta_6$ integrin antagonist is indicated.

The present invention thus provides a compound of formula (I) or a pharmaceutically acceptable salt thereof for use in the treatment of a disease or condition for which an $\alpha_v\beta_6$ integrin antagonist is indicated.

Also provided is the use of a compound of formula (I) or a pharmaceutically acceptable salt thereof in the manufacture of a medicament for the treatment of a disease or condition for which an $\alpha_v\beta_6$ integrin antagonist is indicated.

Also provided is a method of treating a disease or conditions for which an $\alpha_v\beta_6$ integrin antagonist is indicated in a subject in need thereof which comprises administering a therapeutically effective amount of compound of formula (I) or a pharmaceutically acceptable salt thereof.

Suitably the subject in need thereof is a mammal, particularly a human.

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

Fibrotic diseases involve the formation of excess fibrous connective tissue in an organ or tissue in a reparative or reactive process. $\alpha_v\beta_6$ antagonists are believed to be useful in the treatment of a variety of such diseases or conditions including those dependent on $\alpha_v\beta_6$ integrin function and on activation of transforming growth factor beta via alpha v integrins. Diseases may include but are not limited to pulmonary fibrosis (e.g. idiopathic pulmonary fibrosis, non-specific interstitial pneumonia (NSIP), usual interstitial pneumonia (UIP), Hermansky-Pudlak syndrome, progressive massive fibrosis (a complication of coal workers' pneumoconiosis), connective tissue disease-related pulmonary fibrosis, airway fibrosis in asthma and COPD, ARDS associated fibrosis, acute lung injury, radiation-induced fibrosis, familial pulmonary fibrosis, pulmonary hypertension); renal fibrosis (diabetic nephropathy, IgA nephropathy, lupus nephritis, focal segmental glomerulosclerosis (FSGS), transplant nephropathy, autoimmune nephropathy, drug-induced nephropathy, hypertension-related nephropathy, nephrogenic systemic fibrosis); liver fibrosis (virally-induced fibrosis (e.g. hepatitis C or B), autoimmune hepatitis, primary biliary cirrhosis, alcoholic liver disease, non-alcoholic fatty liver disease including non-alcoholic steatohepatitis (NASH), congenital hepatic fibrosis, primary sclerosing cholangitis, drug-induced hepatitis, hepatic cirrhosis); skin fibrosis (hypertrophic scars, scleroderma, keloids, dermatomyositis, eosinophilic fasciitis, Dupytrens contracture, Ehlers-Danlos syndrome, Peyronie's disease, epidermolysis bullosa dystrophica, oral submucous fibrosis); ocular fibrosis (age-related macular degeneration (AMD), diabetic macular oedema, dry eye, glaucoma) corneal scarring, corneal injury and corneal wound healing, prevention of filter bleb scarring post trabeculectomy surgery; cardiac fibrosis (congestive heart failure, atherosclerosis, myocardial infarction, endomyocardial fibrosis, hypertrophic cardiomyopathy (HCM)) and other miscellaneous fibrotic conditions (mediastinal fibrosis, myelofibrosis, retroperitoneal fibrosis, Crohn's disease, neurofibromatosis, uterine leiomyomas (fibroids), chronic organ transplant rejection. There may be additional benefits for additional inhibition of $\alpha_v\beta_1$, $\alpha_v\beta_5$ is or $\alpha_v\beta_8$ integrins In addition, pre-cancerous lesions or cancers associated with $\alpha_v\beta_3$ integrins may also be treated (these may include but are not limited to endometrial, basal cell, liver, colon, cervical, oral, pancreas, breast and ovarian cancers, Kaposi's sarcoma, Giant cell tumours and cancer associated stroma). Conditions that may derive benefit from effects on angiogenesis may also benefit (e.g. solid tumours).

The term "disease or condition for which an $\alpha_v\beta_6$ antagonist is indicated", is intended to include any or all of the above disease states.

In one embodiment the disease or condition for which an $\alpha_v\beta_6$ antagonist is indicated is idiopathic pulmonary fibrosis.

In another embodiment the disease or condition for which an $\alpha_v\beta_6$ antagonist is indicated is selected from corneal scarring, corneal injury and corneal wound healing.

Compositions

While it is possible that for use in therapy, a compound of formula (I) as well as pharmaceutically acceptable salts thereof may be administered as the raw chemical, it is common to present the active ingredient as a pharmaceutical composition.

The present invention therefore provides in a further aspect a pharmaceutical composition comprising a compound of formula (I) or a pharmaceutically acceptable salt and one or more pharmaceutically acceptable carriers, diluents and/or excipients. The compounds of the formula (I) and pharmaceutically acceptable salts are as described above. The carrier(s), diluent(s) or excipient(s) must be acceptable in the sense of being compatible with the other ingredients of the composition and not deleterious to the recipient thereof.

In accordance with another aspect of the invention there is also provided a process for the preparation of a pharmaceutical composition including admixing a compound of the formula (I), or a pharmaceutically acceptable salt thereof, with one or more pharmaceutically acceptable carriers, diluents or excipients. The pharmaceutical composition can be for use in the treatment of any of the conditions described herein.

Further provided is a pharmaceutical composition for the treatment of diseases or conditions for which an $\alpha_v\beta_6$ integrin antagonist is indicated comprising a compound of formula (I) or a pharmaceutically acceptable salt thereof.

Further provided is a pharmaceutical composition comprising 0.01 to 3000 mg of a compound of formula (I) or a pharmaceutical salt thereof and 0.1 to 2 g of one or more pharmaceutically acceptable carriers, diluents or excipients.

Since the compounds of formula (I) are intended for use in pharmaceutical compositions it will be readily understood that they are each preferably provided in substantially pure form, for example, at least 60% pure, more suitably at least 75% pure and preferably at least 85% pure, especially at least 98% pure (% in a weight for weight basis).

Pharmaceutical compositions may be presented in unit dose forms containing a predetermined amount of active ingredient per unit dose. Preferred unit dosage compositions are those containing a daily dose or sub-dose, or an appropriate fraction thereof, of an active ingredient. Such unit doses may therefore be administered more than once a day. Preferred unit dosage compositions are those containing a daily dose or sub-dose (for administration more than once a day), as herein above recited, or an appropriate fraction thereof, of an active ingredient.

Pharmaceutical compositions may be adapted for administration by any appropriate route, for example by the oral (including buccal or sublingual), rectal, inhaled, intranasal, topical (including buccal, sublingual or transdermal), vagina, ocular or parenteral (including subcutaneous, intramuscular, intravenous or intradermal) route. Such compositions may be prepared by any method known in the art of pharmacy, for example by bringing into association the active ingredient with the carrier(s) or excipient(s).

In one embodiment the pharmaceutical composition is adapted for oral administration.

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders suitable for incorporating into tablets or capsules may be prepared by reducing the compound to a suitable fine particle size (e.g. by micronisation) and mixing with a similarly prepared pharmaceutical carrier such as an edible carbohydrate, as, for example, starch or mannitol. Flavouring, preservative, dispersing and colouring agent can also be present.

Capsules may be made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilising agent such as agaragar, calcium carbonate or sodium carbonate can also be added to improve the availability of the medicament when the capsule is ingested.

Moreover, when desired or necessary, suitable binders, glidants, lubricants, sweetening agents, flavours, disintegrating agents and colouring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like.

Lubricants used in these dosage forms include sodium oleate, sodium stearate, magnesium stearate, sodium benzoate, sodium acetate, sodium chloride and the like.

Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an alginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavoured aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavour additive such as peppermint oil or natural sweeteners or saccharin or other artificial sweeteners, and the like can also be added.

Where appropriate, dosage unit compositions for oral administration can be microencapsulated. The formulation can also be prepared to prolong or sustain the release as for example by coating or embedding particulate material in polymers, wax or the like.

The compounds of the invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Pharmaceutical compositions adapted for transdermal administration may be presented as discrete patches intended to remain in intimate contact with the epidermis of the recipient for a prolonged period of time.

Pharmaceutical compositions adapted for topical administration may be formulated as ointments, creams, suspensions, lotions, powders, solutions, pastes, gels, sprays, aerosols or oils.

For treatments of the eye or other external tissues, for example mouth and skin, the compositions are preferably applied as a topical ointment or cream. When formulated in an ointment, the active ingredient may be employed with either a paraffinic or a water miscible ointment base. Alternatively, the active ingredient may be formulated in a cream with an oil-in-water cream base or a water-in-oil base. The compounds of this invention can be administered as topical eye drops. The compounds of this invention can be administered via sub-conjunctival, intracameral or intravitreal routes which would necessitate administration intervals that are longer than daily.

Pharmaceutical formulations adapted for topical administrations to the eye include eye drops wherein the active ingredient is dissolved or suspended in a suitable carrier, especially an aqueous solvent. Formulations to be administered to the eye will have ophthalmically compatible pH and osmolality. One or more ophthalmically acceptable pH adjusting agents and/or buffering agents can be included in a composition of the invention, including acids such as acetic, boric, citric, lactic, phosphoric and hydrochloric acids; bases such as sodium hydroxide, sodium phosphate, sodium borate, sodium citrate, sodium acetate, and sodium lactate; and buffers such as citrate/dextrose, sodium bicarbonate and ammonium chloride. Such acids, bases, and buffers can be included in an amount required to maintain pH of the composition in an ophthalmically acceptable range. One or more ophthalmically acceptable salts can be included in the composition in an amount sufficient to bring osmolality of the composition into an ophthalmically acceptable range. Such salts include those having sodium, potassium or ammonium cations and chloride, citrate, ascorbate, borate, phosphate, bicarbonate, sulfate, thiosulfate or bisulfite anions.

The ocular delivery device may be designed for the controlled release of one or more therapeutic agents with multiple defined release rates and sustained dose kinetics and permeability. Controlled release may be obtained through the design of polymeric matrices incorporating different choices and properties of biodegradable/bioerodable polymers (e.g. poly(ethylene vinyl) acetate (EVA), superhydrolyzed PVA), hydroxyalkyl cellulose (HPC), methylcellulose (MC), hydroxypropyl methyl cellulose (HPMC), polycaprolactone, poly(glycolic) acid, poly(lactic) acid, polyanhydride, of polymer molecular weights, polymer crystallinity, copolymer ratios, processing conditions, surface finish, geometry, excipient addition and polymeric coatings that will enhance drug diffusion, erosion, dissolution and osmosis.

Formulations for drug delivery using ocular devices may combine one or more active agents and adjuvants appropriate for the indicated route of administration. For example, the active agents may be admixed with any pharmaceutically acceptable excipient, lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, and/or polyvinyl alcohol, tableted or encapsulated for conventional administration. Alternatively, the compounds may be dissolved in polyethylene glycol, propylene glycol, carboxymethyl cellulose colloidal solutions, ethanol, corn oil, peanut oil, cottonseed oil, sesame oil, tragacanth gum, and/or various buffers. The compounds may also be mixed with compositions of both biodegradable and non-biodegradable polymers and a carrier or diluent that has a time delay property. Representative examples of biodegradable compositions can include albumin, gelatin, starch, cellulose, dextrans, polysaccharides, poly (D, L-lactide), poly (D, L-lactide-co-glycolide), poly (glycolide), poly (hydroxybutyrate), poly (alkylcarbonate) and poly (orthoesters) and mixtures thereof. Representative examples of non-biodegradable polymers can include EVA copolymers, silicone rubber and poly (methylacrylate), and mixtures thereof.

Pharmaceutical compositions for ocular delivery also include in situ gellable aqueous composition. Such a composition comprises a gelling agent in a concentration effective to promote gelling upon contact with the eye or with lacrimal fluid. Suitable gelling agents include but are not limited to thermosetting polymers. The term "in situ gellable" as used herein includes not only liquids of low viscosity that form gels upon contact with the eye or with lacrimal fluid, but also includes more viscous liquids such as semi-fluid and thixotropic gels that exhibit substantially increased viscosity or gel stiffness upon administration to the eye. See, for example, Ludwig (2005) Adv. Drug Deliv. Rev. 3; 57:1595-639, herein incorporated by reference for purposes of its teachings of examples of polymers for use in ocular drug delivery.

Pharmaceutical compositions adapted for topical administration in the mouth include lozenges, pastilles and mouth washes.

Pharmaceutical compositions adapted for rectal administration may be presented as suppositories or as enemas.

Dosage forms for nasal or inhaled administration may conveniently be formulated as aerosols, solutions, suspensions, gels or dry powders.

Pharmaceutical compositions adapted for vaginal administration may be presented as pessaries, tampons, creams, gels, pastes, foams or spray formulations.

Pharmaceutical compositions adapted for parenteral administration include aqueous and non-aqueous sterile injection solutions which may contain anti-oxidants, buffers, bacteriostats and solutes which render the composition isotonic with the blood of the intended recipient, and aqueous and non-aqueous sterile suspensions which may include suspending agents and thickening agents. The compositions may be presented in unitdose or multi-dose containers, for example sealed ampoules and vials, and may be stored in a freeze-dried (lyophilized) condition requiring only the addition of the sterile liquid carrier, for example water for injections, immediately prior to use.

Extemporaneous injection solutions and suspensions may be prepared from sterile powders, granules and tablets.

Pharmaceutical compositions adapted for sub-cutaneous or intramuscular administration include poly (lactic-co-glycolic acid) (PLGA) copolymer to form microparticles containing the active pharmaceutical ingredient to provide sustain release.

A therapeutically effective amount of a compound of the present invention will depend upon a number of factors including, for example, the age and weight of the subject, the precise condition requiring treatment and its severity, the nature of the formulation, and the route of administration, and will ultimately be at the discretion of the attendant physician or veterinarian. In the pharmaceutical composition, each dosage unit for oral or parenteral administration preferably contains from 0.01 to 3000 mg, more preferably 0.1 to 2000 mg, of a compound of the invention calculated as the zwitterion parent compound.

The pharmaceutically acceptable compounds of the invention can be administered in a daily dose (for an adult patient) of, for example, an oral or parenteral dose of 0.01 mg to 3000 mg per day or 0.5 to 1000 mg per day of the compound of the formula (I) or a pharmaceutically acceptable salt thereof, calculated as the zwitterion. This amount may be given in a single dose per day or more usually in a number (such as two, three, four, five or six) of sub-doses per day such that the total daily dose is the same. An effective amount of a salt thereof may be determined as a proportion of the effective amount of the compound of formula (I) per se.

The compounds of the invention may be employed alone or in combination with other therapeutic agents. Combination therapies according to the present invention thus comprise the administration of at least one compound of formula (I) or a pharmaceutically acceptable salt thereof, and the use of at least one other pharmaceutically active agent. Preferably, combination therapies according to the present invention comprise the administration of at least one compound of formula (I) or a pharmaceutically acceptable salt thereof, and at least one other pharmaceutically active agent. The compound(s) of the invention and the other pharmaceutically active agent(s) may be administered together in a single pharmaceutical composition or separately and, when administered separately this may occur simultaneously or sequentially in any order. The amounts of the compound(s) of the invention and the other pharmaceutically active agent(s) and the relative timings of administration will be selected in order to achieve the desired combined therapeutic effect.

Thus in a further aspect, there is provided a combination comprising a compound of the invention and at least one other pharmaceutically active agent.

Thus in one aspect, the compound and pharmaceutical compositions according to the invention may be used in combination with or include one or more other therapeutic agents, including therapies for allergic disease, inflammatory disease, autoimmune disease, anti-fibrotic therapies and therapies for obstructive airway disease, therapies for diabetic ocular diseases, and therapies for corneal scarring, corneal injury and corneal wound healing.

Anti-allergic therapies include antigen immunotherapy (such as components and fragments of bee venom, pollen, milk, peanut, CpG motifs, collagen, other components of extracellular matrix which may be administered as oral or sublingual antigens), anti-histamines (such as cetirizine, loratidine, acrivastine, fexofenidine, chlorphenamine), and corticosteroids (such as fluticasone propionate, fluticasone furoate, beclomethasone dipropionate, budesonide, ciclesonide, mometasone furoate, triamcinolone, flunisolide, prednisolone, hydrocortisone).

Anti-inflammatory therapies include NSAIDs (such as aspirin, ibuprofen, naproxen), leukotriene modulators (such as montelukast, zafirlukast, pranlukast), and other anti-inflammatory therapies (such as iNOS inhibitors, tryptase inhibitors, IKK2 inhibitors, p38 inhibitors (losmapimod, dilmapimod), elastase inhibitors, beta2 agonists, DP1 antagonists, DP2 antagonists, pI3K delta inhibitors, ITK inhibitors, LP (lysophosphatidic) inhibitors or FLAP (5-lipoxygenase activating protein) inhibitors (such as sodium 3-(3-(tert-butylthio)-1-(4-(6-ethoxypyridin-3-yl)benzyl)-5-((5-methylpyridin-2-yl)methoxy)-1H-indol-2-yl)-2,2-dimethylpropanoate); adenosine a2a agonists (such as adenosine and regadenoson), chemokine antagonists (such as CCR3 antagonists or CCR4 antagonists), mediator release inhibitors.

Therapies for autoimmune disease include DMARDS (such as methotrexate, leflunomide, azathioprine), biopharmaceutical therapies (such as anti-IgE, anti-TNF, anti-interleukins (such as anti-IL-1, anti-IL-6, anti-IL-12, anti-IL-17, anti-IL-18)), receptor therapies (such as etanercept and similar agents); antigen non-specific immunotherapies (such as interferon or other cytokines/chemokines, cytokine/chemokine receptor modulators, cytokine agonists or antagonists, TLR agonists and similar agents).

Other anti-fibrotic therapies includes inhibitors of TGFβ synthesis (such as pirfenidone), tyrosine kinase inhibitors targeting the vascular endothelial growth factor (VEGF), platelet-derived growth factor (PDGF) and fibroblast growth factor (FGF) receptor kinases (such as Nintedanib (BIBF-1120) and imatinib mesylate (Gleevec)), endothelin receptor antagonists (such as ambrisentan or macitentan), antioxidants (such as N-acetylcysteine (NAC); broad-spectrum antibiotics (such as cotrimoxazole, tetracyclines (minocycline hydrochloride)), phosphodiesterase 5 (PDE5) inhibitors (such as sildenafil), anti-αvβx antibodies and drugs (such as anti-αvβ6 monoclonal antibodies (such as those described in WO2003100033A2); intetumumab; cilengitide) may be used in combination.

Therapies for obstructive airway diseases include bronchodilators such as short-acting β2-agonists, such as salbutamol), long-acting β2-agonists (such as salmeterol, formoterol and vilanterol), short-acting muscarinic antagonists (such as ipratropium bromide), long-acting muscarinic antagonists, (such as tiotropium, umeclidinium).

In some embodiments, treatment can also involve combination of a compound of this invention with other existing modes of treatment, for example existing agents for treatment of diabetic ocular diseases, such as anti VEGF therapeutics e.g. Lucentis®, Avastin®, and Aflibercept• and steroids, e.g., triamcinolone, and steroid implants containing fluocinolone acetonide.

In some embodiments, treatment can also involve combination of a compound of this invention with other existing modes of treatment, for example existing agents for treatment of corneal scarring, corneal injury or corneal wound healing, such as Gentel®, calf blood extract, Levofloxacin®, and Ofloxacin®.

The compounds and compositions of the invention may be used to treat cancers alone or in combination with cancer therapies including chemotherapy, radiotherapy, targeted agents, immunotherapy and cell or gene therapy.

It will be clear to a person skilled in the art that, where appropriate, the other therapeutic ingredient(s) may be used in the form of salts, for example as alkali metal or amine salts or as acid addition salts, or prodrugs, or as esters, for example lower alkyl esters, or as solvates, for example hydrates, to optimise the activity and/or stability and/or physical characteristics, such as solubility, of the therapeutic ingredient. It will be clear also that, where appropriate, the therapeutic ingredients may be used in optically pure form.

The combinations referred to above may conveniently be presented for use in the form of a pharmaceutical composition and thus pharmaceutical compositions comprising a combination as defined above together with a pharmaceutically acceptable diluent or carrier represent a further aspect of the invention. The individual compounds of such combinations may be administered either sequentially or simultaneously in separate or combined pharmaceutical compositions. Preferably, the individual compounds will be administered simultaneously in a combined pharmaceutical composition. Appropriate doses of known therapeutic agents will be readily appreciated by those skilled in the art.

It will be appreciated that when the compound of the present invention is administered in combination with one or more other therapeutically active agents normally administered by the inhaled, intravenous, oral, intranasal, ocular topical or other route that the resultant pharmaceutical composition may be administered by the same route. Alternatively, the individual components of the composition may be administered by different routes.

The present inventions will now be illustrated by way of example only.

ABBREVIATIONS

The following list provides definitions of certain abbreviations as used herein. It will be appreciated that the list is not exhaustive, but the meaning of those abbreviations not herein below defined will be readily apparent to those skilled in the art.

Ac (acetyl)
BCECF-AM (2',7'-bis-(2-carboxyethyl)-5-(and -6)-carboxyfluorescein Acetoxymethyl Ester)
BEH (Ethylene Bridged Hybrid Technology)
Bu (butyl)
CBZ (carboxybenzyl)
CHAPS (3-[(3-Cholamidopropyl) dimethylammonio]-1-propanesulfonate)
Chiralcel OD-H (cellulose tris (3, 5-dimethylphenylcarbamate) coated on 5 μm silica gel)
Chiralpak AD-H (amylose tris(3,5-dimethylphenylcarbamate) coated on 5 μm silica gel)
Chiralpak ID (amylose tris(3-chlorophenylcarbamate) immobilised on 5 μm silica gel)
Chiralpak AS (amylose tris((S)-alpha-methylbenzylcarbamate) coated on 5 m silica gel)
CDI (carbonyl diimidazole)
CSH (Charged Surface Hybrid Technology)
CV (column volume)
DCM (dichloromethane)
DIPEA (diisopropylethylamine)
DMF (N, N-dimethylformamide)
DMSO (dimethylsulfoxide)
DSC (differential scanning colorimetry)
Et (ethyl)
EtOH (ethanol)
EtOAc (ethyl acetate)
h (hour/hours)
HCl (Hydrochloric acid)
HEPES (4-(2-hydroxyethyl)-1-piperazineethanesulfonic acid)
LCMS (Liquid Chromatography Mass Spectrometry)
M (molar)
MDAP (mass directed auto-preparative HPLC)
MDCK (Madin-Darby canine kidney)
Me (methyl)
MeCN (acetonitrile)
MeI (methyl iodide)
MeOH (methanol)
min (minute/minutes)
MS (mass spectrum)
$PdCl_2$(dppf)-$CH_2C_2$[1,1'-Bis(diphenylphosphino)ferrocene] dichloropalladium(II), complex with dichloromethane
Ph (phenyl)
$^i$Pr (isopropyl)
(R)-BINAP (R)-(+)-2,2'-Bis (diphenylphosphino)-1,1'-binaphthalene
[Rh (COD) Cl]$_2$(chloro(1,5-cyclooctadiene)rhodium(I) dimer)
SPE (solid phase extraction)
TBME (tert-butyl methyl ether)
TEA (triethylamine)
TFA (trifluoroacetic acid)
TGA (thermal gravimetric analysis)
TGA-IR (thermal gravimetric analyser interfaced with infrared)
THF (tetrahydrofuran)
TLC (thin layer chromatography)
UPLC (Ultra Performance Liquid Chromatography)
XRPD (X-ray powder diffraction)
All references to brine refer to a saturated aqueous solution of sodium chloride.

Experimental Details

Analytical LCMS

Analytical LCMS was conducted on one of the following systems A or B.

The UV detection to all systems was an averaged signal from wavelength of 220 nm to 350 nm and mass spectra were recorded on a mass spectrometer using alternate-scan positive and negative mode electrospray ionization.

Experimental details of LCMS systems A-C as referred to herein are as follows:

System A

Column: 50 mm×2.1 mm ID, 1.7 m Acquity UPLC BEH $C_{18}$ column

Flow Rate: 1 mL/min.

Temp.: 40° C.

Solvents: A: 10 mM ammonium bicarbonate in water adjusted to pH10 with ammonia solution B: Acetonitrile

| Gradient: | Time (min) | A % | B % |
|---|---|---|---|
| | 0 | 99 | 1 |
| | 1.5 | 3 | 97 |
| | 1.9 | 3 | 97 |
| | 2.0 | 99 | 1 |

System B

Column: 50 mm×2.1 mm ID, 1.7 μm Acquity UPLC BEH C18 column

Flow Rate: 1 mL/min

Temp.: 40° C.

Solvents: A: 0.1% v/v solution of formic acid in water

B: 0.1% v/v solution of formic acid in acetonitrile

| Gradient: | Time (min) | A % | B % |
|---|---|---|---|
| | 0 | 97 | 3 |
| | 1.5 | 0 | 100 |
| | 1.9 | 0 | 100 |
| | 2.0 | 97 | 3 |

System C

Column: 50 mm×2.1 mm ID, 1.7 μm Acquity UPLC CSH C18 column

Flow Rate: 1 mL/min.

Temp.: 40° C.

Solvents: A: 10 mM ammonium bicarbonate in water adjusted to pH10 with ammonia solution B: Acetonitrile

| Gradient: | Time (min) | A % | B % |
|---|---|---|---|
| | 0 | 97 | 3 |
| | 1.5 | 5 | 95 |
| | 1.9 | 5 | 95 |
| | 2.0 | 97 | 3 |

Intermediate 1: 7-(Bromomethyl)-1, 2, 3, 4-tetrahydro-1, 8-naphthyridine (Compound (XV))

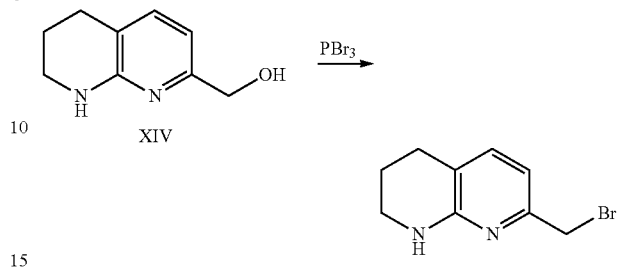

Phosphorus tribromide (0.565 mL, 5.99 mmol) was added dropwise to a suspension of (5, 6, 7, 8-tetrahydro-1, 8-naphthyridin-2-yl) methanol (Compound (XIV)): see US20040092538, page 80, [0844]) (820 mg, 4.99 mmol) in anhydrous acetonitrile (50 mL) at 0° C. under nitrogen. Upon addition a deep orange coloured precipitate formed, which turned to pale orange. The reaction mixture was stirred at 0° C. for 1 h by which time the reaction was complete. The mixture was concentrated in vacuo and the residue was partitioned between ethyl acetate (250 mL) and a saturated aqueous solution of $NaHCO_3$ (250 mL). The aqueous phase was further extracted with ethyl acetate (250 mL). The combined organic solutions were passed through a hydrophobic frit and then concentrated in vacuo to give the title compound (1.05 g, 93%) as a fluffy creamy solid: LCMS (System C) RT=0.95 min, ES+ve m/z 227, 229 $(M+H)^+$.

Intermediate 2: Triphenyl ((5, 6, 7, 8-tetrahydro-1, 8-naphthyridin-2-yl) methyl) phosphonium bromide (Compound (XVI))

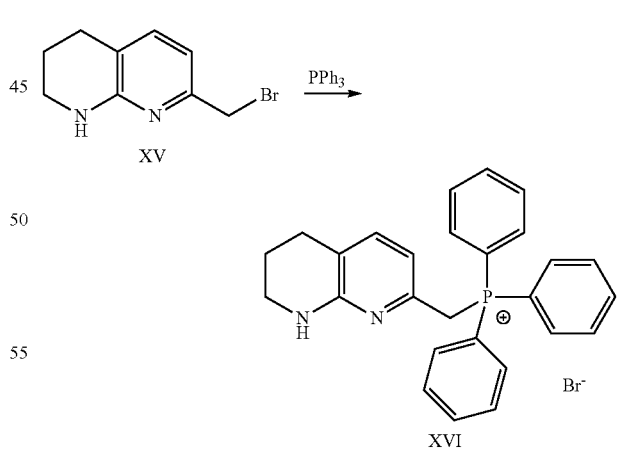

A solution of 7-(bromomethyl)-1, 2, 3, 4-tetrahydro-1, 8-naphthyridine (Compound (XV), for a preparation see Intermediate 1) (1.00 g, 4.40 mmol) in acetonitrile (98 mL) was treated with triphenylphosphine (1.270 g, 4.84 mmol) and the solution was stirred at room temperature under nitrogen overnight. The mixture was concentrated in vacuo to give a dark cream solid, which was then triturated with diethyl ether to give the title compound (2.139 g, 99%) as a pale cream solid: LCMS (System C) RT=1.23 min, ES+ve m/z 409 (M+H)⁺.

Intermediate 3: (E, Z) Benzyl 3-fluoro-3-(2-(5, 6, 7, 8-tetrahydro-1, 8-naphthyridin-2-yl) vinyl) pyrrolidine-1-carboxylate. (Compound (VIII))

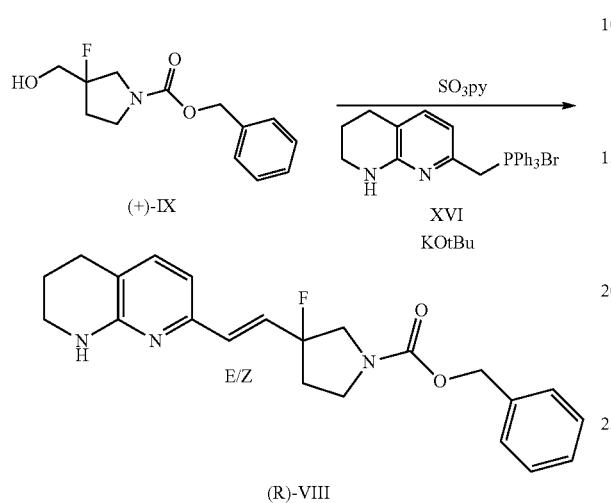

A stirred solution of (+)-benzyl 3-fluoro-3-(hydroxymethyl) pyrrolidine-1-carboxylate (Compound (IX): available from Wuxi App Tec) (260 mg, 1.03 mmol) in DCM (3 mL) and DMSO (0.3 mL), under nitrogen, was treated with DIPEA (0.896 mL, 5.13 mmol). After cooling to 0-5° C. (ice bath) pyridine sulfur trioxide (327 mg, 2.05 mmol) was added portionwise over ca. 5 min to oxidise the alcohol compound (IX) to the corresponding aldehyde compound (X) which was not isolated. The cooling bath was removed and stirring was continued for 0.5 h. Meanwhile a solution of triphenyl ((5, 6, 7, 8-tetrahydro-1, 8-naphthyridin-2-yl) methyl) phosphonium bromide (Compound (XVI), for a preparation see Intermediate 2) (553 mg, 1.13 mmol) in anhydrous DCM (10 mL), under nitrogen, was treated dropwise with potassium tert-butoxide (1M in THF) (1.232 mL, 1.232 mmol) over ca. 5 min resulting in an orange coloured solution. Stirring was continued for 10 min and then the aldehyde (formula (X)) solution was added to the ylide solution in one shot and the mixture was stirred at ambient temperature for 22 h. The reaction mixture was diluted with DCM (20 mL), washed with saturated aqueous sodium bicarbonate (20 mL) and brine (20 mL), dried (Na₂SO₄) then evaporated in vacuo. The dark brown residue was purified by chromatography on a 20 g silica SPE cartridge and eluted with a gradient of 0-100% ethyl acetate-cyclohexane over 30 min to obtain the title compound as two geometrical isomers:

Isomer 1: a straw-coloured gum (123.4 mg, 31%); LCMS (System A) RT=1.28 min, 95%, ES+ve m/z 382 (M+H)⁺ and Isomer 2: a straw-coloured gum (121.5 mg, 31%); LCMS (System A) RT=1.22 min, 91%, ES+ve m/z 382 (M+H)⁺

Overall yield=244.9 mg, 62.5%.

The configuration of Intermediate 3 was subsequently shown to be (R) and the two geometrical isomers are: (R,E)-benzyl 3-fluoro-3-(2-(5,6,7,8-tetrahydro-1,8-naphthyridin-2-yl)vinyl)pyrrolidine-1-carboxylate and (R,Z)-benzyl 3-fluoro-3-(2-(5,6,7,8-tetrahydro-1,8-naphthyridin-2-yl)vinyl)pyrrolidine-1-carboxylate.

Intermediate 4: Benzyl 3-fluoro-3-(2-(5,6,7,8-tetrahydro-1,8-naphthyridin-2-yl)ethyl)pyrrolidine-1-carboxylate (Compound (VII))

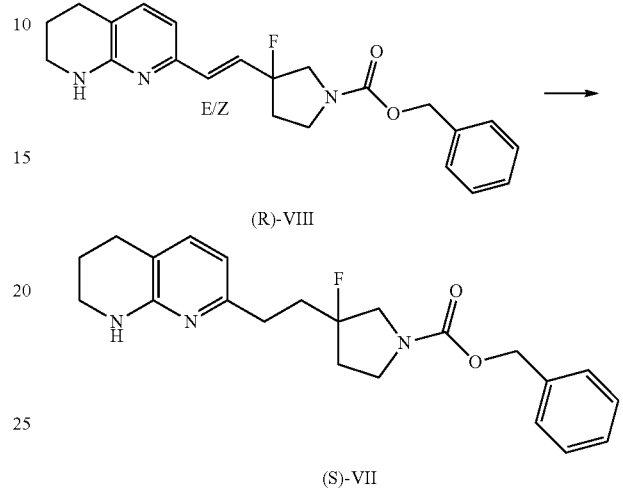

A solution of (E/Z) benzyl 3-fluoro-3-(2-(5,6,7,8-tetrahydro-1,8-naphthyridin-2-yl)vinyl)pyrrolidine-1-carboxylate (Compound VIII, for a preparation see Intermediate 3) (1:1, E:Z) (244 mg, 0.640 mmol) in DMF (2 mL) was treated with benzenesulphonyl hydrazide (available from Alfa Aesar) (275 mg, 1.60 mmol) and potassium carbonate (354 mg, 2.56 mmol). The reaction mixture was heated to 130° C. for 1 h, then allowed to cool and partitioned between DCM and water. The organic phase was washed with water and dried through a hydrophobic frit. The organic solution was evaporated in vacuo and the residual orange oil was purified by chromatography on a silica cartridge (20 g) eluting with a gradient of 0-50% [(3:1 EtOAc:EtOH)-EtOAc] over 20 min. The appropriate fractions were combined and evaporated in vacuo to give the title compound (150 mg, 61%) as a pale yellow gum: LCMS (System A) RT=1.24 min, 90%, ES+ve m/z 384 (M+H)⁺. The absolute configuration of Intermediate 4 was subsequently shown by inference to be (S) hence the compound is (S)-benzyl 3-fluoro-3-(2-(5,6,7,8-tetrahydro-1,8-naphthyridin-2-yl)ethyl)pyrrolidine-1-carboxylate. The change from (R) in Intermediate 3 to (S) in Intermediate 4 is due to the change in priority on removal of the double bond.

Intermediate 5: 7-(2-(3-Fluoropyrrolidin-3-yl)ethyl)-1,2,3,4-tetrahydro-1,8-naphthyridine (Compound (V))

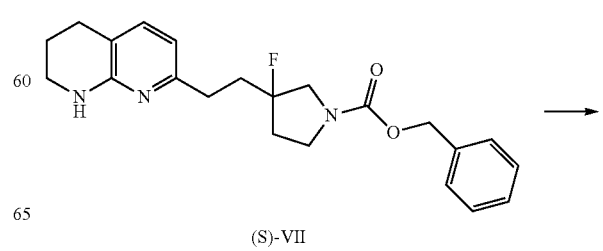

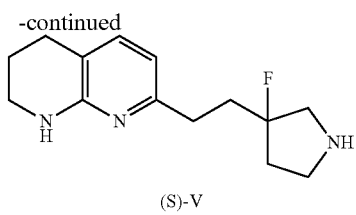

(S)-V

A stirred solution of benzyl 3-fluoro-3-(2-(5,6,7,8-tetrahydro-1,8-naphthyridin-2-yl)ethyl)pyrrolidine-1-carboxylate (Compound (VII, for a preparation see Intermediate 4) (4.67 g, 12.2 mmol) in ethanol (70 mL) containing 10% palladium on carbon (0.50 g) was stirred under a hydrogen atmosphere for 7 h. LCMS showed incomplete deprotection and additional 10% palladium on carbon (0.25 g) was added and the mixture was stirred under a hydrogen atmosphere overnight. The reaction mixture existed as a dark grey suspension so DCM was added to dissolve up the material until the mixture became black. The catalyst was removed by filtration through a pad of celite and the filtrate and washings were evaporated in vacuo. The residue was evaporated from DCM to obtain the title compound as an orange oil (3.28 g): LCMS (System A) RT=0.79 min, 90%, ES+ve m/z 250 (M+H)+. The configuration of Intermediate 5 was subsequently established by inference as (S) and the name of the compound is (S)-7-(2-(3-fluoropyrrolidin-3-yl)ethyl)-1,2,3,4-tetrahydro-1,8-naphthyridine.

Intermediate 6 [7-(2-(3-Fluoropyrrolidin-3-yl)ethyl)-1,2,3,4-tetrahydro-1,8-naphthyridine, (Compound (V)) Methanesulfonic Acid Salt

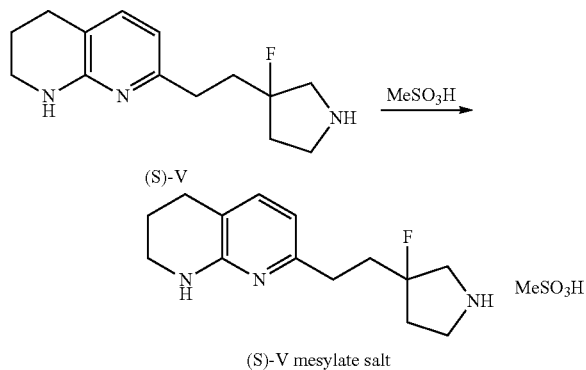

This salt of compound (V) may be prepared and crystallised as a method of purification of compound (V) above.

2-Butanol (5 mL) was added to 7-(2-(3-fluoropyrrolidin-3-yl) ethyl)-1,2,3,4-tetrahydro-1,8-naphthyridine (Compound (V), for a preparation see Intermediate 5) (1.0 g, 4.0 mmol) and the mixture was heated until complete dissolution was achieved. Methanesulfonic acid (0.260 mL, 4.01 mmol) was added to the warm solution and the mixture was heated to 80° C. with stirring. The solution was then allowed to cool to ambient temperature. No precipitation was evident immediately, so the solution was cooled further in a fridge (ca. 4° C.). After 3 days, a significant amount of solid was observed. The solid was isolated by filtration and washed with cold 2-butanol, and dried further in vacuo to afford the title compound (600 mg, 43%) as a pale yellow solid: LCMS (System A) RT=0.80 min, 100%, ES+ve m/z 250 (M+H)+;

Analytical Chiral HPLC on a Chiralpak AD column (250 mm×4.6 mm) RT=8.41 min, 99.6% and RT=12.03 min, 0.4%, eluting with 40% EtOH-heptane (containing 0.2% isopropylamine), flow rate 1 mL/min, detecting at 235 nm. The configuration of Intermediate 6 was subsequently established by inference as (S) and the name of the compound is (S)-7-(2-(3-fluoropyrrolidin-3-yl)ethyl)-1,2,3,4-tetrahydro-1,8-naphthyridine methanesulfonic acid salt.

Intermediate 7: (E)-Methyl 4-acetoxybut-2-enoate (Compound (VI))

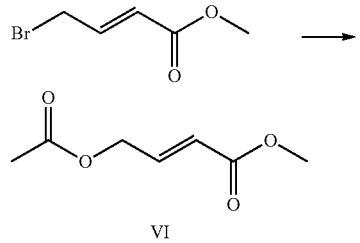

A suspension of sodium acetate (3.5 g, 42 mmol) in MeCN (30 mL) was treated with methyl 4-bromocrotonate (available from Aldrich) (3.33 mL, 5 g, 28 mmol) and the mixture was heated to 50° C. for 3 d. The mixture was diluted with ether and then filtered. The solid was washed with ether and the combined filtrate and washings were evaporated under reduced pressure. After evaporation the residue was partitioned between ether and water. The organic phase was washed with aqueous sodium bicarbonate, dried over MgSO$_4$, and evaporated under reduced pressure to give a pale orange oil. NMR indicated a mixture of product and starting material, therefore, sodium acetate (3.44 g, 42 mmol) was added to the residual oil, followed by MeCN (10 mL) and the mixture was heated to 70° C. over the weekend. The mixture was concentrated under reduced pressure and the residue was partitioned between ether and water. The organic solution was washed with water, brine, dried (MgSO$_4$) and filtered. The filtrate was evaporated under reduced pressure to give the title compound (3.55 g, 80%) as an orange oil: NMR δ (CDCl$_3$) 6.92 (1H, dt, J 16, 5 Hz), 6.01 (1H, dt, J 16, 2 Hz), 4.72 (2H, dd, J 5, 2 Hz), 3.73 (3H, s), 2.10 (3H, s).

Intermediate 8: (E)-Methyl 4-(3-fluoro-3-(2-(5,6,7,8-tetrahydro-1,8-naphthyridin-2-yl)ethyl)pyrrolidin-1-yl)but-2-enoate (Compound (III)

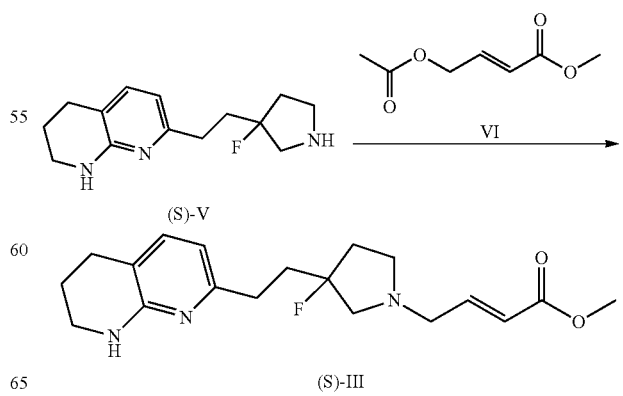

A mixture of (E)-methyl 4-acetoxybut-2-enoate (compound (VI), for a preparation see Intermediate 7) (127 mg, 0.802 mmol), 7-(2-(3-fluoropyrrolidin-3-yl)ethyl)-1,2,3,4-tetrahydro-1,8-naphthyridine (compound (V), for a preparation see Intermediate 5) (200 mg, 0.802 mmol) and $PdCl_2$ (dppf)-$CH_2Cl_2$ adduct (65.7 mg, 0.080 mmol) in DCM (2 mL) was stirred at ambient temperature for 2 h. LCMS showed around 50% conversion and DIPEA (0.279 mL, 1.60 mmol) was added and the solution stirred for 2 h at room temperature. LCMS showed almost complete conversion to the product. The material was loaded directly onto a column and purified by chromatography (20 g amino propyl cartridge) eluting with a gradient of 0-100% EtOAc in cyclohexane over 20 min. The appropriate fractions were combined and evaporated to give the title compound (101.4 mg, 36% yield): LCMS (System C) RT=1.08 min, 95%, ES+ve m/z 348 (M+H)$^+$. The configuration of Intermediate 8 was established by inference as (S) and the name as (S,E)-methyl 4-(3-fluoro-3-(2-(5,6,7,8-tetrahydro-1,8-naphthyridin-2-yl)ethyl)pyrrolidin-1-yl)but-3-enoate.

Intermediate 9: Methyl 4-(3-fluoro-3-(2-(5,6,7,8-tetrahydro-1,8-naphthyridin-2-yl)ethyl)pyrrolidin-1-yl)-3-(3-morpholinophenyl)butanoate. Isomer A and Isomer B)

was filtered through celite, washed with EtOAc (10 mL) and concentrated. The reaction mixture was suspended in MeOH (300 μL) and purified by reverse phase chromatography (C18, 40 g, 5-95% MeCN (containing 0.1% ammonia) in 10 mM ammonium bicarbonate, 20 CV). The appropriate fractions were combined and evaporated to give a diastereomeric mixture of the title Compound (II) (99 mg, 58%) as a gum.

The mixture was dissolved in EtOH (2 mL) and heptane (1 mL) and the diastereoisomers were separated by chiral HPLC on a Chiralcel OD-H column (3 cm×25 cm) eluting with 30% EtOH (containing 0.2% isopropylamine)—70% heptane (flow rate=30 mL/min, detecting at 215 nm) to give the two diastereoisomers of the Compound (II).

Isomer A (17 mg, 10%): Analytical chiral HPLC RT=8.0 min, >99.5% on Chiralcel OD-H column (4.6 mm id×25 cm) eluting with (30% EtOH (containing 0.2% isopropylamine)-heptane, flow rate=1.0 mL/min, detecting at 215 nm; LCMS (System A) RT=1.21 min, 99%, ES+ve m/z 511 (M+H)$^+$; $^1$H NMR (400 MHz, CD$_3$OD) δ 7.17 (t, J=7.5 Hz, 1H), 7.13 (d, J=7.5 Hz, 1H), 6.88-6.84 (m, 1H), 6.76 (d, J=7.5 Hz, 1H), 6.38 (d, J=7.5 Hz, 1H), 3.87-3.81 (m, 4H), 3.58 (s, 3H), 3.42-3.36 (m, 2H), 3.17-3.10 (m, 4H), 2.90-2.49 (m, 12H), 2.11-1.84 (m, 6H), 1.38-1.28 (m, 2H).

Isomer B (77 mg, 45%): Analytical chiral HPLC RT=17.2 min, >99.5% on Chiralcel OD-H column (4.6 mm id×25 cm)

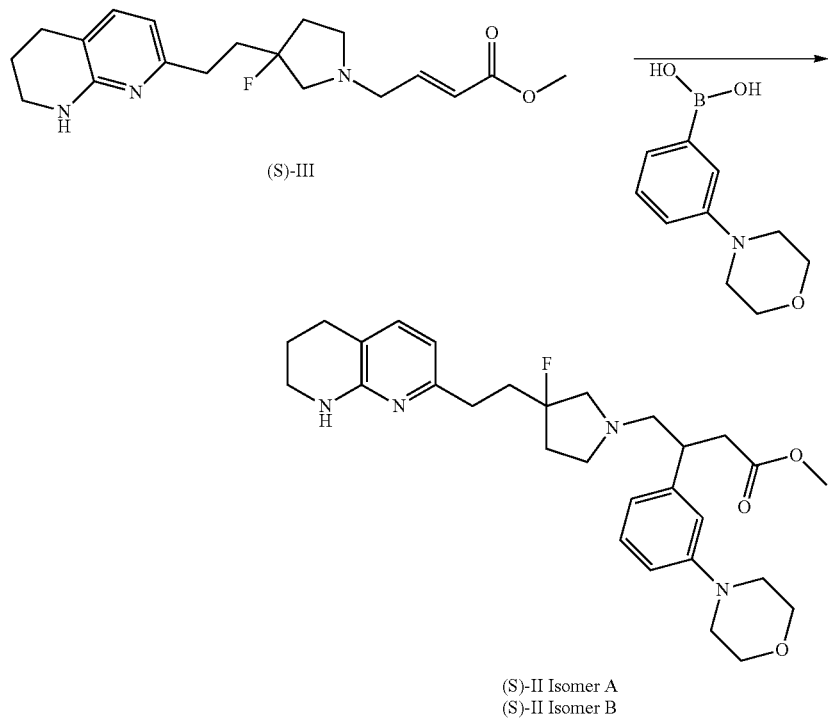

(S)-III

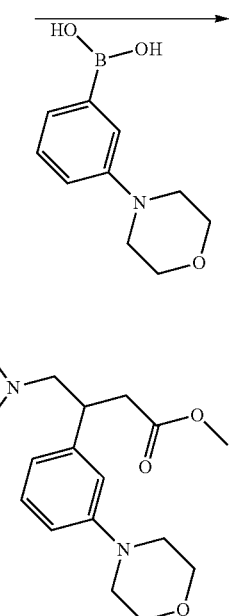

(S)-II Isomer A
(S)-II Isomer B (E)-Methyl 4-(3-fluoro-3-(2-(5,6,7,8-tetrahydro-1,8-naphthyridin-2-yl)ethyl)pyrrolidin-1-yl)but-2-enoate (Compound (III), for a preparation see Intermediate 8) (145 mg, 0.334 mmol), (R)-BINAP (31 mg, 0.05 mmol), [Rh(COD)Cl]$_2$ (10 mg, 0.020 mmol), (3-morpholinophenyl)boronic acid (available from for example CombiBlocks, Manchester Organics or Fluorochem) (259 mg, 1.251 mmol) and 3.8M KOH (0.22 mL, 0.836 mmol) were dissolved in 1,4-dioxane (2 mL) in a microwave vial and the solution was heated in a microwave oven (100 min, 95° C.). The reaction mixture eluting with (30% EtOH (containing 0.2% isopropylamine)-heptane, flow rate=1.0 mL/min, detecting at 215 nm; $^1$H NMR (400 MHz, CD$_3$OD) δ 7.18 (t, J=7.5 Hz, 1H), 7.13-7.07 (m, 1H), 6.89-6.77 (m, 2H), 6.74 (d, J=7.5 Hz, 1H), 6.36 (d, J=7.5 Hz, 1H), 3.87-3.75 (m, 4H), 3.57 (s, 3H), 3.40-3.34 (m, 2H), 3.28-3.20 (m, 1H), 3.16-3.07 (m, 4H), 2.91-2.74 (m, 4H), 2.74-2.44 (m, 9H), 2.07-1.91 (m, 3H), 1.91-1.80 (m, 2H).

The absolute configuration of the two isomers of Intermediate 9 was established subsequently by inference to be for the major isomer (Isomer B) (S)-methyl 4-((S)-3-fluoro-3-(2-(5,6,7,8-tetrahydro-1,8-naphthyridin-2-yl)ethyl)pyrrolidin-1-yl)-3-(3-morpholinophenyl)butanoate and for the minor isomer (Isomer A) (R)-methyl 4-((S)-3-fluoro-3-(2-(5,6,7,8-tetrahydro-1,8-naphthyridin-2-yl)ethyl)pyrrolidin-1-yl)-3-(3-morpholinophenyl)butanoate.

Intermediate 10: (S, E, Z)-Benzyl 3-fluoro-3-(2-(5, 6, 7, 8-tetrahydro-1, 8-naphthyridin-2-yl) vinyl) pyrrolidine-1-carboxylate. (Compound (XXIII))

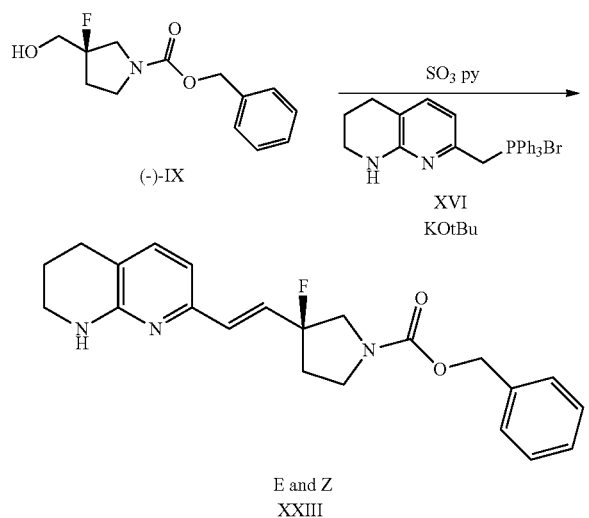

A stirred solution of (R)-(−)-benzyl 3-fluoro-3-(hydroxymethyl)pyrrolidine-1-carboxylate [(−)-compound (IX)] (available from Wuxi App Tec) (4.18 g, 16.50 mmol) in dichloromethane (60 mL) and DMSO (5.86 mL, 83 mmol) was treated with DIPEA (14.41 mL, 83 mmol) under nitrogen. After cooling to 0-5° C. in an ice bath, pyridine sulfur trioxide (5.40 g, 33.9 mmol) was added portion wise over ca. 5 min: The solution turned a pale yellow colour and stirring was continued for ca. 0.5 h to give a yellow solution. The solution was washed with dilute HCl (50 mL) and dried (MgSO$_4$). Then triphenyl((5,6,7,8-tetrahydro-1,8-naphthyridin-2-yl)methyl)phosphonium bromide (compound XVI, for a preparation see Intermediate 2) (8.06 g, 16.47 mmol) and a small amount of DCM (ca. 5 mL) were added before the addition of cyclohexane (3.81 mL) to give a pale orange solution. Potassium tert-butoxide (19.80 mL, 19.80 mmol) was added dropwise to this solution which resulted in a cream coloured suspension. After 1 h the reaction mixture was diluted with DCM (200 mL), washed with saturated aqueous sodium bicarbonate (200 mL) and brine (200 mL), dried (MgSO$_4$), then evaporated in vacuo. The dark orange oil solidified overnight and was triturated with diethyl ether (ca. 30 mL), then filtered to give a cream solid and a yellow filtrate. The filtrate was evaporated in vacuo to give an orange oil and this was applied to a 330 g normal phase silica cartridge and eluted with a cyclohexane/ethyl acetate gradient (0-100% ethyl acetate over 50 min). Appropriate fractions were evaporated in vacuo to give the title compound (3.953 g, 63%) as a straw coloured gum: LCMS (System C) RT=1.28 min, 50% and 1.34 min, 46% ES+ve m/z 382 (M+H)$^+$.

Intermediate 11: (R)-Benzyl 3-fluoro-3-(2-(5,6,7,8-tetrahydro-1,8-naphthyridin-2-yl)ethyl)pyrrolidine-1-carboxylate

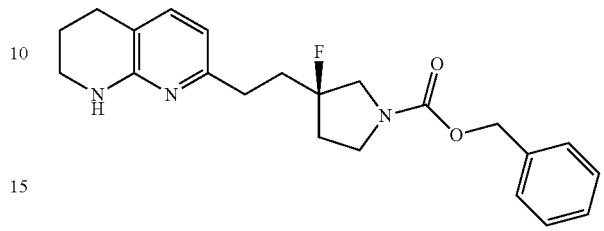

A stirred solution of (S, E and Z)-benzyl 3-fluoro-3-(2-(5,6,7,8-tetrahydro-1,8-naphthyridin-2-yl)vinyl)pyrrolidine-1-carboxylate (Compound XXIII, for a preparation see Intermediate 10) (3.814 g, 10.00 mmol) in DMF (40 mL) was treated under nitrogen with potassium carbonate (5.53 g, 40.0 mmol), followed by benzenesulfonohydrazide (4.38 g, 25.4 mmol) to give a yellow liquid. The mixture was heated at 100° C. for 1 h, then allowed to cool to ambient temperature and filtered through celite. The filtrate was evaporated in vacuo to give a cream coloured slurry. This was partitioned between water (100 mL) and ethyl acetate (100 mL) and the organic layer further washed with water (4×100 mL), dried (MgSO$_4$), and then evaporated in vacuo to obtain a yellow oil (3.261 g). This was left on high vacuum line over the weekend (2.982 g). The oil was dissolved in the minimum of DMSO (ca. 3 mL) and applied to a 120 g reverse phase cartridge and eluted with a gradient of 10-100% (acetonitrile containing 0.1% NH$_3$) in 10 mM aqueous ammonium bicarbonate over 12 CV. Fractions 6-9 were partially evaporated in vacuo to remove the acetonitrile. The remaining solution was diluted with water (40 mL) and DCM (60 mL), then separated. The aqueous layer was further extracted with DCM (3×30 mL) and the organic extracts were combined, dried (MgSO$_4$) and then evaporated in vacuo to give the title compound (2.145 g, 56%) as a pale yellow oil. LCMS (System C): RT=1.25 min, ES+ve m/z 384 (M+H)$^+$.

Intermediate 12: (R)-7-(2-(3-fluoropyrrolidin-3-yl)ethyl)-1,2,3,4-tetrahydro-1,8-naphthyridine

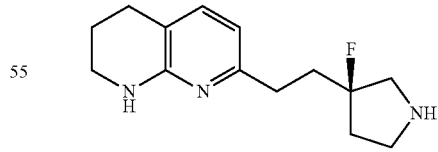

A solution of (R)-benzyl 3-fluoro-3-(2-(5,6,7,8-tetrahydro-1,8-naphthyridin-2-yl)ethyl)pyrrolidine-1-carboxylate (for a preparation see Intermediate 11) (2.334 g, 6.09 mmol) in ethanol (50 mL) was added to 10% Palladium on carbon (250 mg, 0.235 mmol) and the mixture stirred under a hydrogen atmosphere for 3 h at which point more palladium on carbon (107.2 mg) was added. The reaction was stirred overnight. DCM (ca. 30 mL) was added and the mixture filtered through celite under nitrogen. The filtrate was evaporated in vacuo to give the title compound (1.575 g) as a yellow oil: LCMS (System C) RT=0.83 min, ES+ve m/z 250 (M+H)+.

Intermediate 13: (R,E)-Methyl 4-(3-fluoro-3-(2-(5, 6,7,8-tetrahydro-1,8-naphthyridin-2-yl)ethyl)pyrrolidin-1-yl)but-2-enoate

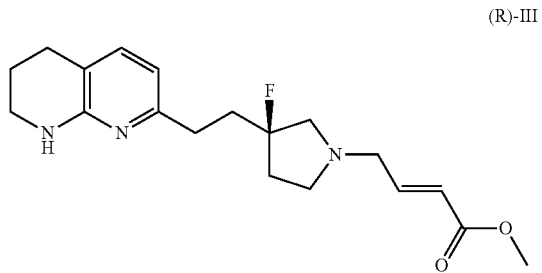 [SMILES: COC(=O)/C=C/CN1CC[C@](F)(CCc2ccc3c(n2)NCCC3)C1]

(R)-III (E)-methyl 4-acetoxybut-2-enoate (0.951 g, 6.01 mmol) (Compound (IV), for a preparation see Intermediate 7), (R)-7-(2-(3-fluoropyrrolidin-3-yl)ethyl)-1,2,3,4-tetrahydro-1,8-naphthyridine (for a preparation see Intermediate 12) (1.520 g, 6.10 mmol), PdCl$_2$(dppf)-CH$_2$Cl$_2$ adduct (0.242 g, 0.331 mmol) and potassium acetate (2.083 g, 21.22 mmol) were dissolved in DCM (25 mL) and the reaction mixture was stirred under nitrogen for 20 h to give an orange liquid (2.188 g). The reaction mixture was partitioned between DCM (50 mL) and water (50 mL) and extracted once more with DCM (50 mL). The combined organic phases were washed with brine (50 mL) and dried over MgSO$_4$. The solvent was removed in vacuo and the residue was dissolved in DCM and purified on an aminopropyl cartridge (50 g) using a gradient of 0-100% ethyl acetate-cyclohexane over 20 min. The appropriate fractions were combined and evaporated in vacuo to give the title compound (1.59 g, 75%) as a yellow oil. LCMS (System C): RT=1.07 min, ES+ve m/z 348 (M+H)+.

Intermediate 14. Methyl (R)-4-((R)-3-fluoro-3-(2-(5,6,7,8-tetrahydro-1,8-naphthyridin-2-yl)ethyl)pyrrolidin-1-yl)-3-(3-morpholinophenyl)butanoate and methyl (S)-4-((R)-3-fluoro-3-(2-(5,6,7,8-tetrahydro-1,8-naphthyridin-2-yl)ethyl)pyrrolidin-1-yl)-3-(3-morpholinophenyl)butanoate

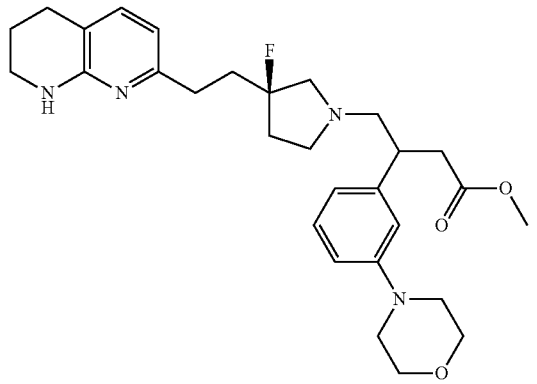

(R)-II Isomer 1, Isomer 2

(R,E)-Methyl 4-(3-fluoro-3-(2-(5,6,7,8-tetrahydro-1,8-naphthyridin-2-yl)ethyl)pyrrolidin-1-yl)but-2-enoate (for a preparation see Intermediate 13) (429 mg, 0.988 mmol), [Rh(COD)Cl]$_2$ (29.7 mg, 0.060 mmol), (3-morpholinophenyl)boronic acid (716 mg, 3.46 mmol) and 3.8 M KOH (0.647 mL, 2.46 mmol) were dissolved in 1,4-dioxane (2 mL) and the solution was heated in a microwave reactor (high power, 100 min, 95° C.). The reaction mixture was filtered through celite, washed with EtOAc (10 mL) and concentrated. The reaction mixture was suspended in MeOH (300 µL) and purified by reverse phase chromatography (C18, 40 g) eluting with a gradient of 30-85% MeCN (containing 0.1% ammonia) in 10 mM aqueous ammonium bicarbonate, 30 CV). The appropriate fractions were combined and evaporated to give the product as a mixture of diastereoisomers (214 mg, 42% yield). The mixture was separated by preparative chiral HPLC on a Chiralcel OD-H column (30 mm×25 cm) eluting with 30% EtOH (containing 0.2% isopropylamine) in heptane, flow rate=30 mL/min, detecting at 215 nm to give the two diastereoisomers of the title compound:

Isomer 1 Methyl (R)-4-((R)-3-fluoro-3-(2-(5,6,7,8-tetrahydro-1,8-naphthyridin-2-yl)ethyl)pyrrolidin-1-yl)-3-(3-morpholinophenyl)butanoic acid (29 mg, 6%) LCMS (System B) RT=0.54 min, ES+ve m/z 511 (M+H)+; Analytical chiral HPLC RT=7.5 min, >99.5% on a Chiralcel OD-H column (4.6 mm×25 cm) eluting with 30% EtOH containing 0.2% isopropylamine-heptane, flow-rate 1 mL/min.

Isomer 2 Methyl (S)-4-((R)-3-fluoro-3-(2-(5,6,7,8-tetrahydro-1,8-naphthyridin-2-yl)ethyl)pyrrolidin-1-yl)-3-(3-morpholinophenyl)butanoic acid (138 mg, 27%): LCMS (System B) RT=0.57 min, ES+ve m/z 511 (M+H)+; Analytical chiral HPLC RT=13.9 min, >99.5% on a Chiralcel OD-H column (4.6 mm×25 cm) eluting with 30% EtOH containing 0.2% isopropylamine-heptane, flow-rate 1 mL/min.

Intermediate 15. 4-(4-Fluoro-3-(4,4,5,5-tetramethyl-1,3,2-dioxaborolan-2-yl)phenyl)morpholine

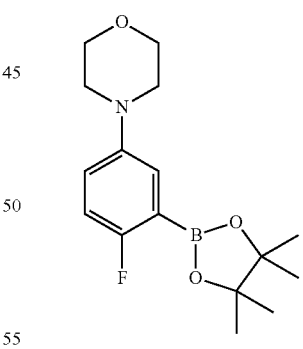

4-(4-Fluorophenyl)morpholine (Roiban, G-D. Eur. J. Org. Chem. 2014, 2070-2076) (85 g, 469 mmol) was dissolved in cyclohexane (1.2 L) and the flask was purged for 30 min with argon. To the resulting solution under argon were added [Ir(COD)OMe]$_2$ (31.1 g, 46.9 mmol), 4,4'-di-tert-butyl-2,2'-bipyridine (25.2 g, 94 mmol) and 4,4,5,5-tetramethyl-1,3,2-dioxaborolane (60.0 g, 469 mmol) and stirred at 70° C. for 18 h. Reaction was monitored by TLC. (10% EtOAc in hexane. Rf=0.2, detecting with UV). Ethyl acetate (500 mL) and brine (200 mL) were added to the reaction mixture and the organic phase was separated. The aqueous phase was extracted with ethyl acetate (2×300 mL). The combined organic phases were washed with water, brine, dried (Na$_2$SO$_4$), filtered and concentrated under reduced pressure. The residual liquid (80 g) was loaded to a silica gel (100-200 mesh) column eluting with 3% EtOAc-Hexane. Appropriate fractions were combined and evaporated in vacuo. The residue (60 g) was triturated with pentane (100 mL) to afford 55 g of product, which was further triturated with cold pentane to give the title compound (50.3 g, 35%) as a white solid: LCMS ES+ve m/z 308 (M+H)$^+$.

Intermediate 16. (S) Methyl 4-(S)-(3-fluoro-3-(2-(5, 6,7,8-tetrahydro-1,8-naphthyridin-2-yl)ethyl)pyrrolidin-1-yl)-3-(2-fluoro-5-morpholinophenyl)butanoate

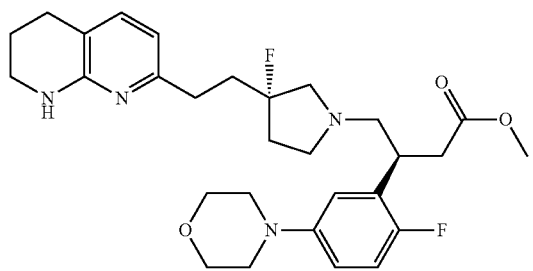 [SMILES: COC(=O)C[C@H](CN1CC[C@@](F)(CCc2ccc3c(n2)NCCC3)C1)c1cc(N2CCOCC2)ccc1F]

A flask was charged with (2-fluoro-5-morpholinophenyl) boronic acid (for a preparation see Intermediate 15) (216 mg, 0.958 mmol), (S,E)-methyl 4-(3-fluoro-3-(2-(5,6,7,8-tetrahydro-1,8-naphthyridin-2-yl)ethyl)pyrrolidin-1-yl)but-2-enoate (for a preparation see Intermediate 8) (111 mg, 0.319 mmol) and KOH (aq) (0.252 mL, 0.958 mmol) in 1,4-dioxane (3 mL). The solution was degassed using nitrogen. [Rh(COD)Cl]$_2$ (7.88 mg, 0.016 mmol) and (R)-BINAP (23.87 mg, 0.038 mmol) were dissolved in 1,4-dioxane (3 mL) and the solution was degassed. The two solutions were mixed, degassed, and heated under nitrogen at 90° C. for 1 h. LCMS showed minimal conversion to the product but still a lot of both starting materials remained. [Rh(COD)Cl]$_2$ (7.88 mg, 0.016 mmol) and (R)-BINAP (23.87 mg, 0.038 mmol) were added to the solution and the solution heated to 50° C. for 2 h). LCMS showed further conversion to the product, but conversion was still only around 20%. Further quantities of (R)-BINAP (23.87 mg, 0.038 mmol), [Rh (COD)Cl]$_2$ (7.88 mg, 0.016 mmol), (2-fluoro-5-morpholinophenyl)boronic acid (216 mg, 0.958 mmol) and KOH (aq) (0.252 mL, 0.958 mmol) were added. The solution was heated at 50° C. for 2 h. LCMS showed further conversion to the required product and so the reaction was halted. The reaction mixture was passed through celite (10 g) and washed with 3CV of MeOH. The filtrate was evaporated under reduced pressure. The residue was purified via reverephase chromatography on Biotage SNAP cartridge (30 g) eluting with 40-85% acetonitrile—10 mM aq. ammonium bicarbonate solution. The appropriate fractions were collected and evaporated under vacuum to yield the title compound (116.9 mg, 69%). LCMS (System A) RT=1.23 min, 94%, ES+ve m/z 529 (M+H)$^+$; Anal. Chiral HPLC RT=9.5 min, >95% eluting with 20% EtOH (containing 0.2% isopropylamine)-heptane on a Chiralcel OD-H (250 mm×4.6 mm) chromatography column, flow-rate 1 mL/min, detecting at 215 nm.

PREPARATION OF EXAMPLES

Example 1: (S)-4-((S)-3-Fluoro-3-(2-(5,6,7,8-tetrahydro-1,8-naphthyridin-2-yl)ethyl)pyrrolidin-1-yl)-3-(3-morpholinophenyl)butanoic acid

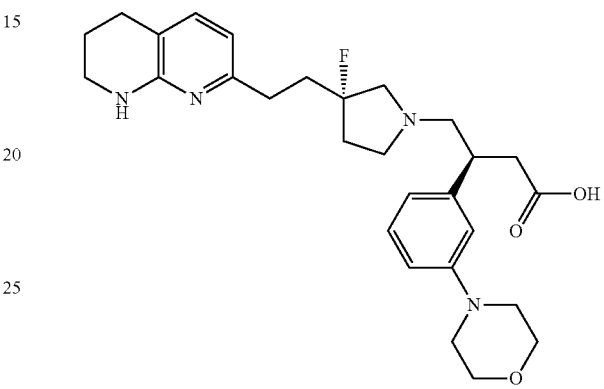

(S)-Methyl 4-((S)-3-fluoro-3-(2-(5,6,7,8-tetrahydro-1,8-naphthyridin-2-yl)ethyl)pyrrolidin-1-yl)-3-(3-morpholinophenyl)butanoate (for a preparation see Intermediate 9, Isomer B) (77 mg, 0.15 mmol) was dissolved in MeOH (1 mL). LiOH$_{(aq)}$ (1 M, 0.452 mL) was added to the reaction mixture. The reaction mixture was stirred for 18 h at ambient temperature. HCl$_{(aq)}$ (2 M, 0.226 mL) was added to the reaction mixture, then it was loaded onto a pre-conditioned SCX column eluting with MeOH (2 CV) and then with 2 M NH$_3$ in MeOH (2 CV). The ammoniacal fractions were combined and evaporated. The residue was purified using reverse phase chromatography (C18, 5-95% MeCN (containing 0.1% ammonia) in 10 mM ammonium bicarbonate, 15 CV). The appropriate fractions were collected and evaporated to give the title compound as a gum (61 mg, 81% yield): Analytical chiral HPLC RT=7.06 min, >99.5% on a Chiralpak AS-H column (4.6 mm id×25 cm) eluting with 50% EtOH-heptane, flow rate=1.0 mL/min, detecting at 215 nm; LCMS (System A) RT=0.76 min, 98%, ES+ve m/z 497 (M+H)$^+$; $^1$H NMR (CD$_3$OD, 600 MHz) 7.27-7.20 (m, 2H), 6.89 (s, 1H), 6.86 (dd, J=8.3, 2.0 Hz, 1H), 6.78 (d, J=7.7 Hz, 1H), 6.45 (d, J=7.3 Hz, 1H), 3.88-3.80 (m, 4H), 3.49-3.28 (m, 6H), 3.25-3.18 (m, 2H), 3.17-3.13 (m, 4H), 3.03 (d, J=8.1 Hz, 1H), 2.82 (dd, J=16.1, 8.8 Hz, 1H), 2.77-2.68 (m, 4H), 2.67-2.56 (m, 1H), 2.25 (d, J=3.3 Hz, 1H), 2.20-2.09 (m, 3H), 1.90 (quin, J=6.0 Hz, 2H).

The absolute configuration of the asymmetric centres of Example 1 was determined and the compound was found to be of structural formula (IA2) (S)-4-((S)-3-fluoro-3-(2-(5, 6, 7, 8-tetrahydro-1, 8-naphthyridin-2-yl) ethyl) pyrrolidin-1-yl)-3-(3-morpholinophenyl) butanoic acid.

Example 2: (S)-4-(R)-(3-Fluoro-3-(2-(5,6,7,8-tetrahydro-1,8-naphthyridin-2-yl)ethyl)pyrrolidin-1-yl)-3-(3-morpholinophenyl)butanoic acid

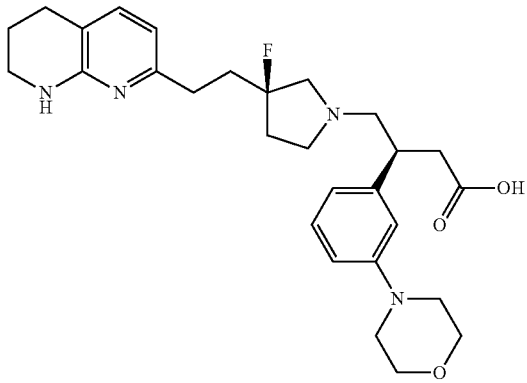 [SMILES: O=C(O)C[C@H](CN1CC[C@](F)(CCc2ccc3c(n2)NCCC3)C1)c1cccc(N2CCOCC2)c1]

A solution of methyl (S)-4-(R)-(3-fluoro-3-(2-(5,6,7,8-tetrahydro-1,8-naphthyridin-2-yl)ethyl)pyrrolidin-1-yl)-3-(3-morpholinophenyl)butanoate (for a preparation see Intermediate 14 Isomer 2) (138 mg, 0.270 mmol) in methanol (1 mL) was treated with aqueous LiOH solution (1 M, 0.811 mL) and the reaction mixture was stirred for 18 h at ambient temperature. 2 M HCl (0.405 mL, 0.811 mmol) was then added to the reaction mixture, and applied to a pre-conditioned SCX cartridge. The cartridge was then washed with MeOH (2 CV), followed by 2 M ammonia in methanol (2 CV). The ammoniacal fractions were combined, evaporated and the residue was purified using reverse phase chromatography (C18 cartridge) eluting with 5-95% MeCN (containing 0.1% ammonia) in aqueous 10 mM ammonium bicarbonate solution (15 CV). The appropriate fractions were evaporated to give the title compound (121 mg, 90%) as a gum. The gum was dissolved in diethyl ether (2 mL) and then cyclohexane (~5 mL) was added dropwise. A solid appeared and the suspension was evaporated under reduced pressure to give the title compound. LCMS (System A) RT=0.77 min, ES+ve m/z 497 (M+H)$^+$; $^1$H NMR (DMSO-$d_6$, 600 MHz) 7.12 (t, J=7.5 Hz, 1H), 7.02 (d, J=7.5 Hz, 1H), 6.82-6.81 (m, 1H), 6.76-6.73 (m, 1H), 6.69-6.67 (m, 1H), 6.28 (d, J=7.5 Hz, 1H), 6.26-6.24 (m, 1H), 3.74-3.69 (m, 4H), 3.25-3.21 (m, 2H), 3.15-3.09 (m, 1H), 3.09-3.05 (m, 4H), 2.87-2.65 (m, 4H), 2.64-2.56 (m, 3H), 2.56-2.45 (m, 4H+(obscured by solvent)), 2.40 (dd, J=16, 8.5 Hz, 1H), 2.04-1.81 (m, 4H), 1.74 (quin, J=6.0 Hz, 2H).

The absolute configuration of the asymmetric centres of Example 2 was determined and the compound was found to be of structural formula (IA3) (S)-4-(R)-(3-fluoro-3-(2-(5, 6, 7, 8-tetrahydro-1, 8-naphthyridin-2-yl) ethyl) pyrrolidin-1-yl)-3-(3-morpholinophenyl) butanoic acid.

Example 3: (S)-4-(S)-(3-Fluoro-3-(2-(5,6,7,8-tetrahydro-1,8-naphthyridin-2-yl)ethyl)pyrrolidin-1-yl)-3-morpholinophenyl)butanoic acid maleate salt MeCN (0.2 mL) was added to (S)-4-(S)-(3-fluoro-3-(2-(5,6,7,8-tetrahydro-1,8-naphthyridin-2-yl)ethyl)pyrrolidin-1-yl)-3-(3-morpholinophenyl)butanoic acid (for a preparation see Example 1) (19.8 mg) followed by addition of maleic acid (3M solution in water, 0.0133 mL). The temperature of the solution was cycled between 40 and 5° C. for 48 h with an hour hold between each cycle. The crystalline solids were isolated using a centrifuge filter tube fitted with 0.45·m filter yielding crystalline maleate salt.

MeCN (3.5 mL) was added to (S)-4-(S)-(3-fluoro-3-(2-(5,6,7,8-tetrahydro-1,8-naphthyridin-2-yl)ethyl)pyrrolidin-1-yl)-3-(3-morpholinophenyl)butanoic acid (for a preparation see Example 1) (349.6 mg, 0.70 mmol). To the oily solution, maleic acid (3 M solution in water, 1.0 equivalent) was added which led to an orange solution. Seeds of crystals (for a preparation see above) were added. The solution was stirred at 40° C. for 1 h, cooled to 5° C. for 1 h and stirred at room temperature overnight. Crystalline maleate salt was isolated by vacuum filtration and air-dried for 15 min. The yield of crystalline maleate salt was (269.6 mg, 62%): mp 184.5° C. (melting onset, DSC).

Alternative preparation: To (S)-4-((S)-3-fluoro-3-(2-(5,6,7,8-tetrahydro-1,8-naphthyridin-2-yl)ethyl)pyrrolidin-1-yl)-3-(3-morpholinophenyl)butanoic acid (for a preparation see Example 1) (1.146 g, 2.308 mmol) was added acetonitrile (11.5 mL). To this stirred oily solution was added 3.0M maleic acid in water (0.769 mL, 2.308 mmol) to give a pale orange solution. The solution was heated to 40° C. and seeds of crystalline maleate (for a preparation, see above) were added. The mixture was heated at 40° C. for 1 h and the white solid that appeared went pale pink over the hour. The mixture was cooled in an ice/water bath for 1 h. The suspension was stirred at room temperature for 18 h and then the solid was collected by filtration, washed with acetonitrile (2 mL), and dried in vacuo to give the title compound (751 mg, 53%) as a pale pink solid. $^1$H NMR (DMSO-$d_6$, 600 MHz) 7.27 (1H, d, CH), 7.17 (1H, t, CH), 6.92 (1H, br.s, NH), 6.89 (1H, t, CH), 6.80 (1H, dd, CH), 6.75 (1H, br.d, CH), 6.44 (1H, d, CH), 6.04 (2H, s, CH [maleate]), 3.73 (4H, br.t, 2×CH2), 3.31 (2H, t, CH2), 3.29-3.20 (2H, CH+½ CH2), 3.17-3.07 (7H, br.t+m, 2×CH2+3×½ CH2), 3.04 (1H, br.m, ½ CH2), 2.98 (1H, br.m, ½ CH2), 2.75 (1H, dd, ½ CH2), 2.68-2.59 (4H, m, 2×CH2), 2.49 (1H, dd, ½ CH2), 2.17-1.98 (4H, m, 2×CH2), 1.78 (2H, m, CH2).

Example 4: (S)-4-(S)-(3-Fluoro-3-(2-(5,6,7,8-tetrahydro-1,8-naphthyridin-2-yl)ethyl)pyrrolidin-1-yl)-3-(3-morpholinophenyl)butanoic acid fumarate salt MeCN (0.2 mL) was added to (S)-4-(S)-(3-fluoro-3-(2-(5,6,7,8-tetrahydro-1,8-naphthyridin-2-yl)ethyl)pyrrolidin-1-yl)-3-(3-morpholinophenyl)butanoic acid (for a preparation see Example 1) (19.7 mg) followed by addition of fumaric acid (0.2M solution in EtOH, 198.3 µL). The temperature of the solution was cycled between 40° C. and 5° C. for 48 h with an hour hold between each cycle. The solvent was evaporated under reduced pressure and MeCN (0.2 mL) was added. The temperature of the product was cycled between 40° C. and 5° C. overnight (~16 h) with an hour hold between each cycle which led to a gum. Seeds of maleate salt (for a preparation see Example 3) were added the gum and the suspension was stirred at room temperature overnight which led to a mixture of gum and crystalline solids EtOH (0.5 mL) was added to (S)-4-(S)-(3-fluoro-3-(2-(5,6,7,8-tetrahydro-1,8-naphthyridin-2-yl)ethyl)pyrrolidin-1-yl)-3-(3-morpholinophenyl)butanoic acid (for a preparation see Example 1) (344.2 mg, 0.69 mmol). To the oily solution, fumaric acid (0.2 M solution in EtOH, 1.0 equivalent) was added along with seeds of fumarate salt (for a preparation see above) which led to an off-white precipitate. The suspension was stirred at 40° C. for 1 h, cooled to 5° C. for 1 h and stirred at room temperature overnight. Crystalline fumarate salt was isolated by vacuum filtration and air-dried for 15 min. The yield of crystalline fumarate salt was (345.9 mg, 81%): mp 171. ° C. (melting onset, DSC).

Alternative Preparation:

To (S)-4-((S)-3-fluoro-3-(2-(5,6,7,8-tetrahydro-1,8-naphthyridin-2-yl)ethyl)pyrrolidin-1-yl)-3-(3-morpholinophenyl)butanoic acid (for a preparation see Example 1) (1.24 g, 2.50 mmol) was added EtOH (1.8 mL). To this stirred oily solution was added 0.2M fumaric acid in EtOH (12.48 mL, 2.5 mmol) and seeds of crystalline fumarate salt (for a preparation see above) to give a pale orange solution and a gum. This was heated to 40° C. for 1 h. A white solid precipitated over the hour. The suspension was cooled in an ice/water bath and stirred for 1 h. The suspension was then stirred at room temperature for 18 h. The solid was collected by filtration, washed with ethanol (2 mL). The solid was dried in vacuo to give the title compound (1.34 g, 88%) as a white solid: $^1$H NMR (DMSO-$d_6$, 600 MHz) 7.13 (1H, t, CH), 7.08 (1H, d, CH), 6.82 (1H, t, CH), 6.78 (1H, br.s, NH), 6.75 ppm (1H, dd, CH), 6.69 (1H, br.d, CH), 6.61 (2H, s, CH [fumarate]), 6.31 (1H, d, CH), 3.72 (4H, br.t, 2×CH2), 3.25 (2H, br.t, CH2), 3.13 (1H, m, CH), 3.08 (4H, br.t, 2×CH2), 2.85-2.69 (5H, m, CH2+3× ½ CH2), 2.61 (2H, t, CH2), 2.58-2.48 (4H, m, CH2+2×½CH2), 2.41 (1H, dd, CH), 2.03-1.85 (4H, m, 2×CH2), 1.75 (2H, m, CH2).

Example 5. (S)-4-((S)-3-Fluoro-3-(2-(5,6,7,8-tetrahydro-1,8-naphthyridin-2-yl)ethyl)pyrrolidin-1-yl)-3-(2-fluoro-5-morpholinophenyl)butanoic acid

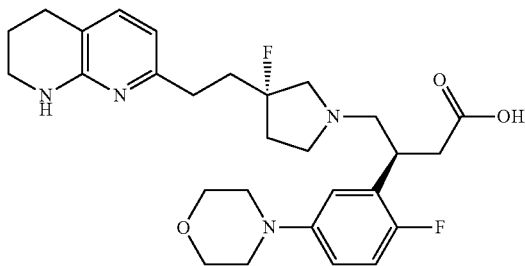 [SMILES: O=C(O)C[C@H](CN1CC[C@@](F)(CCc2ccc3c(n2)NCCC3)C1)c1cc(N2CCOCC2)ccc1F]

A solution of (S) methyl 4-((S)-3-fluoro-3-(2-(5,6,7,8-tetrahydro-1,8-naphthyridin-2-yl)ethyl)pyrrolidin-1-yl)-3-(2-fluoro-5-morpholinophenyl)butanoate (for a preparation see Intermediate 16) (116.9 mg, 0.221 mmol) in THF, was treated with aq. LiOH (1 M, 1.1 mL, 1.1 mmol). The solution was stirred at 25° C. for 5 h. LCMS showed complete conversion to the product. To the solution was added 2 M HCl (0.663 mL, 1.327 mmol) and then the solution was loaded onto a preconditioned SCX column (10 g) eluting with 3 CV 2M NH$_3$ in MeOH (3 CV). The appropriate fraction was collected and evaporated under reduced pressure to give the title compound (114.3 mg, 100%) as a pink solid: LCMS (System A) RT=0.77 min, 98%, ES+ve m/z 515 (M+H)$^+$; NMR (D$_2$O, 400 MHz) 7.37 (d, J=7 Hz, 1H), 7.06 (t, J=9 Hz, 1H), 6.99-6.92 (m, 2H), 6.49 (d, J=7 Hz, 1H), 3.88-3.80 (m, 4H), 3.67-3.39 (m), 3.36-3.20 (m), 3.10-3.03 (m, 4H), 2.76-2.62 (m, 5H), 2.51 (dd, J=15, 7 Hz, 1H), 2.38-2.07 (m, 4H), 1.85-1.77 (m, 2H).

Example 6. (S)-4-(S)-(3-Fluoro-3-(2-(5,6,7,8-tetrahydro-1,8-naphthyridin-2-yl)ethyl)pyrrolidin-1-yl)-3-(3-morpholinophenyl)butanoic acid citrate salt hydrate MeCN (0.2 mL) was added to (S)-4-((S)-3-fluoro-3-(2-(5,6,7,8-tetrahydro-1,8-naphthyridin-2-yl)ethyl)pyrrolidin-1-yl)-3-(3-morpholinophenyl)butanoic acid (for a preparation see Example 1) (20.4 mg) followed by addition of citric acid (1M solution in THF, 41.1 µL) which led to a gum. The temperature of the gum residue was cycled between 40° C. and 5° C. for 48 h with an hour hold between each cycle. The solvent was evaporated under reduced pressure and MeCN (0.2 mL) was added. The temperature of the obtained product was cycled between 40° C. and 5° C. overnight (~16 h) with an hour hold between each cycle which led to crystalline citrate salt.

MeCN (6.0 mL) was added to a sample of (S)-4-((S)-3-fluoro-3-(2-(5,6,7,8-tetrahydro-1,8-naphthyridin-2-yl)ethyl)pyrrolidin-1-yl)-3-(3-morpholinophenyl)butanoic acid (for a preparation see Example 1) (349.5 mg). To the oily solution, citric acid (1M solution in THF, 0.704 mL) was added in five aliquots which led to a gummy material. Seeds of crystalline citrate salt (for a preparation see above) were added. The gummy suspension was stirred at 40° C. for an hour, cooled to 5° C. for an hour and stirred at room temperature overnight, followed by cycling the temperature of the suspension between 40° C. and 5° C. for two days. Crystalline citrate salt was isolated by vacuum filtration and air-dried for 15 min. The yield of crystalline citrate salt was (315.9 mg, 65%): mp 121.4° C. (melting onset by DSC). TGA data showed about 2.7% wt. loss between 25 and 135° C. TGA-IR analysis of the evolving gases revealed the presence of water indicating the citrate salt was a hydrate (theoretical % wt for 1 equivalent of water is 2.6%).

Crystalline mesylate and disuccinate salts were prepared similarly from acetone-toluene and acetonitrile, respectively, and also found to be hydrated.

Example 7. (R)-4-((S)-3-Fluoro-3-(2-(5,6,7,8-tetrahydro-1,8-naphthyridin-2-yl)ethyl)pyrrolidin-1-yl)-3-(3-morpholinophenyl)butanoic acid

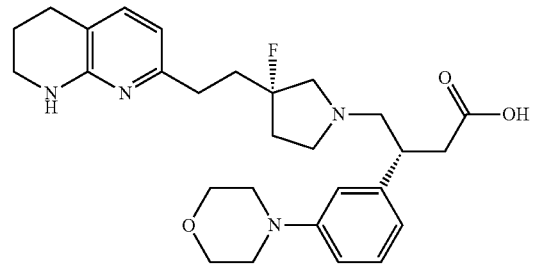 [SMILES: O=C(O)C[C@@H](CN1CC[C@@](F)(CCc2ccc3c(n2)NCCC3)C1)c1cccc(N2CCOCC2)c1]

Into a microwave vial (0.5-2 ml) were added (E)-methyl 4-bromobut-2-enoate (for a preparation see Intermediate 7) (113 mg, 0.634 mmol), (S)-7-(2-(3-fluoropyrrolidin-3-yl)ethyl)-1,2,3,4-tetrahydro-1,8-naphthyridine (for a preparation see Intermediate 5) (166.4 mg, 0.667 mmol), DIPEA (0.233 mL, 1.33 mmol) and dichloromethane (1 mL) at 0° C. The solution was stirred at 0° C. for 3 h. LCMS showed reasonable conversion to the alkylated intermediate. The solution was then evaporated under nitrogen. To the microwave vial was added 3.8 M KOH (aq) (0.351 mL, 1.335 mmol, [Rh(COD)Cl]$_2$ (15 mg, 0.030 mmol), (3-morpholinophenyl)boronic acid (276 mg, 1.335 mmol) and R-BINAP (50 mg, 0.080 mmol) and the vial placed in the microwave (5 h, 50° C., high power). LCMS showed some conversion and that both the starting material and the boronic acid were still present. The vial was placed in the microwave again (1 h, 70° C.). LCMS showed further conversion to the ester and complete protodeborylation of the boronic acid. R-BINAP (50 mg, 0.080 mmol), [Rh(COD)Cl]$_2$ (15 mg, 0.030 mmol), (3-morpholinophenyl)boronic acid (276 mg, 1.335 mmol) and 3.8 M KOH (aq) (0.351 mL, 1.33 mmol) were added to the vial and the vial was placed in the microwave (1 h, 85° C.). LCMS showed some conversion but to improve the yield further R-BINAP (50 mg, 0.080 mmol), [Rh(COD)Cl]$_2$ (15 mg, 0.030 mmol), (3-morpholinophenyl)boronic acid (276 mg, 1.335 mmol) and 3.8 M KOH (aq) (0.351 mL, 1.33 mmol) were added and the vial placed in the microwave again (1 h, 100° C.). LCMS showed sufficient conversion and the mixture was passed through celite (10 g, 20 mL MeOH) and the filtrate was evaporated under vacuum. The sample was loaded in MeOH:DMSO (1:1) and purified on a reverse phase (C18) column (30 g) using a 50-95% MeCN (containing 0.1% ammonia) in 10 mM ammonium bicarbonate) gradient over 10 CV. The appropriate fractions were combined and evaporated in vacuo to give the required intermediate. To the round bottom flask was added 3.8 M KOH (3.34 mL, 12.69 mmol) and the solution suspended in tetrahydrofuran (2 mL) (stirred over night, 25° C.). LCMS showed minimal conversion to the carboxylate. 1 M LiOH (aq) (3.34 mL, 3.34 mmol) was added and the reaction stirred at 25° C. 2M HCl (aq) (8.34 mL, 16.68 mmol) was added to the reaction mixture and it was then loaded onto a pre-wetted SCX column (10 g, pre wet with 1 CV MeOH, then 1 CV MeCN) and then washed with 2 CV MeCN followed by 2 CV NH$_3$ in MeOH. The appropriate fraction was evaporated under reduced pressure. The sample was dissolved in 10:10:1 MeOH:DMSO:H$_2$O (2.4 mL) and purified by MDAP (conducted on an XBridge C$_{18}$ column (typically 100 mm×30 mm i.d. 5 μm packing diameter) at ambient temperature, eluting with a gradient of acetonitrile—10 mM aqueous ammonium bicarbondate adjusted to pH10 with ammonia solution). The solvent was evaporated under a stream of nitrogen to give the required product as a mixture of diastereoisomers. The mixture was separated by preparative chiral HPLC on a Daicel Chiralpak AS column (20 mm×250 mm) eluting with 50% EtOH in heptane at a flow rate of 15 mL/min, detecting at 215 nm. The solvent was evaporated from fractions containing the minor, later eluting isomer to give the title compound (7 mg, 2%). Analytical chiral HPLC RT=8.15 min on a Daicel Chiralpak AS column (4.6 mm×25 cm) eluting with 50% EtOH in heptane, flow rate=1.0 mL/min, detecting at 215 nm; LCMS (System C) RT=0.76 min, 98.9%, ES+ve m/z 497 (M+H)$^+$.

Example 8. (R)-4-((R)-3-Fluoro-3-(2-(5,6,7,8-tetrahydro-1,8-naphthyridin-2-yl)ethyl)pyrrolidin-1-yl)-3-(3-morpholinophenyl)butanoic acid

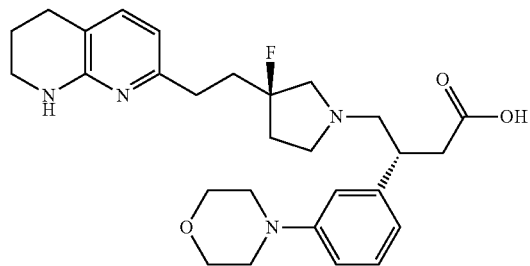

(R,E)-Methyl 4-(3-fluoro-3-(2-(5,6,7,8-tetrahydro-1,8-naphthyridin-2-yl)ethyl)pyrrolidin-1-yl)but-2-enoate (for a preparation see Intermediate 13) (110 mg, 0.253 mmol) was dissolved in 1,4-dioxane (2 mL) under nitrogen. (3-Morpholinophenyl)boronic acid (157 mg, 0.760 mmol) was then added to the reaction mixture. [Rh(COD)Cl]$_2$ (13.4 mg, 0.027 mmol) was dissolved in 1,4-dioxane (1 mL) and nitrogen was bubbled through for 2 min. This dark red solution was added to the main reaction flask. 3.8 M KOH (aq) (0.2 mL, 0.76 mmol) was added, then the reaction mixture was heated to 50° C. for 1 h. LCMS showed some conversion to the product. The reaction mixture was stirred at 50° C. for 1 h. LCMS showed no further conversion to the product. The reaction mixture was cooled and filtered through celite. The column was washed with EtOH (10 mL). The solution was evaporated under reduced pressure then suspended in 1 M LiOH (aq) (1 mL, 1 mmol) and 1,4-dioxane (1 mL). The reaction mixture was stirred overnight. LCMS showed conversion to the product. The reaction mixture was acidified with 2 M HCl (aq) (0.5 mL). The crude mixture was loaded onto an SCX cartridge and eluted with 2M NH$_3$ in MeOH. The ammoniacal fractions were evaporated and the crude mixture was suspended in MeOH (1 mL). The material was purified by reverse phase chromatography on a C18 column (30 g) eluting with a gradient of 5-70% MeCN (containing 0.1% ammonia) in 10 mM ammonium bicarbonate, 10 CV). The appropriate fractions were combined and evaporated. The residue was purified by chiral HPLC on a Daicel Chiralpak AS column (20 mm×25 cm) eluting with 50% EtOH in heptane at a flow rate of 15 mL/min and detecting at 215 nm. The solvent was evaporated from fractions containing the later eluting isomer to give the title compound (6 mg, 5%). Analytical chiral HPLC RT=26.5 min on a Daicel Chiralpak AS-H column (4.6 mm×25 cm) eluting with 50% EtOH in heptane, flow rate=1.0 mL/min, detecting at 215 nm; LCMS (System A) RT=0.81 min, 100%, ES+ve m/z 497 (M+H)$^+$.

Example 9. 4-((R)-3-Fluoro-3-(2-(5,6,7,8-tetrahydro-1,8-naphthyridin-2-yl)ethyl)pyrrolidin-1-yl)-3-(2-fluoro-5-morpholinophenyl)butanoic acid

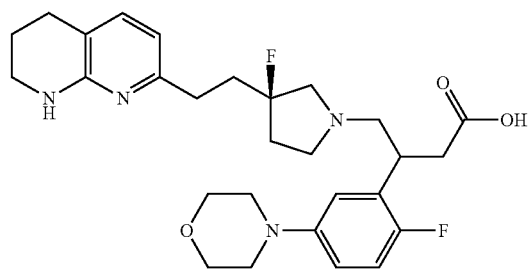 [SMILES: O=C(O)CC(CN1CC[C@](F)(CCc2ccc3c(n2)NCCC3)C1)c1cc(N2CCOCC2)ccc1F]

(R, E)-Methyl 4-(3-fluoro-3-(2-(5,6,7,8-tetrahydro-1,8-naphthyridin-2-yl)ethyl)pyrrolidin-1-yl)but-2-enoate (for a preparation see Intermediate 13) (145 mg, 0.417 mmol), [Rh(COD)Cl]$_2$ (10.29 mg, 0.021 mmol), R-BINAP (31.2 mg, 0.050 mmol), 4-(4-fluoro-3-(4,4,5,5-tetramethyl-1,3,2-dioxaborolan-2-yl)phenyl)morpholine (for a preparation see Intermediate 15) (256 mg, 0.835 mmol) and 3.8 M KOH (aq) (0.220 mL, 0.835 mmol) were dissolved in 1,4-dioxane (2 mL) and the solution was heated in the microwave (high power, 1 h, 100° C.). The solution was left over the weekend and LCMS showed no conversion to the product. The reaction was repeated with added R-BINAP (31.2 mg, 0.050 mmol), [Rh(COD)Cl]$_2$ (10.29 mg, 0.021 mmol) and 3.8 M KOH (aq) (0.220 mL, 0.835 mmol). LCMS showed the reaction had progressed sufficiently and the mixture was passed through celite (MeOH, 3CV) and evaporated under reduced pressure. The product was purified by reverse phase chromatography (loaded in 1:1 MeOH/DMSO) on a C18 (40 g) column, eluting with 35-95% MeCN (containing 0.1% ammonia) in 10 mM ammonium bicarbonate (10CV). Appropriate fractions were evaporated under reduced pressure and the product was then dissolved in tetrahydrofuran (2 mL) and reacted with 1 M LiOH (aq) (2.087 mL, 2.087 mmol) (room temperature, 2 h). LCMS showed the reaction had progressed to completion. 2M HCl (aq) (1.5 mL, 3 mmol) was added and the mixture was loaded onto a pre-wetted SCX column (10 g, pre conditioned with 1CV MeOH, then 1CV MeCN, sample loaded, washed with 2CV MeCN, then 2CV of 2M $NH_3$ in MeOH). The appropriate fraction was evaporated under reduced pressure. The product was loaded onto a reverse phase C18 column (12 g) eluting with 15-55% MeCN (containing 0.1% ammonia) in 10 mM ammonium bicarbonate (10CV). The appropriate fractions were evaporated under reduced pressure to give the title compound (12 mg, 6%). LCMS (System A) RT=0.77 min, 98%, ES+ve m/z 515 $(M+H)^+$.

Biological Assays

Cell Adhesion Assays

Reagents and methods utilised were as described [Ludbrook et al, *Biochem. J.* 2003, 369, 311 and Macdonald et al. *ACS Med Chem Lett* 2014, 5, 1207-1212 for $\alpha_v\beta_8$ assay), with the following points of clarification. The following cell lines were used, with ligands in brackets: K562-$\alpha_v\beta_3$ (LAP-$b_1$), K562-$\alpha_v\beta_5$ (Vitronectin), K562-$\alpha_v\beta_6$ (LAP-$b_1$), K562-$\alpha_v\beta_8$ (LAP-$b_1$), A549-$\alpha_v\beta_1$ (LAP-$b_1$). The divalent cation used to facilitate adhesion was 2 mM $MgCl_2$. Adhesion was quantified by cell labelling with the fluorescent dye BCECF-AM (Life Technologies), where cell suspensions at $3\times10^6$ cells/mL were incubated with 0.33 uL/mL of 30 mM BCECF-AM at 37° C. for 10 minutes, then 50 μL/well were dispensed into the 96-well assay plate. At the assay conclusion cells that adhered were lysed using 50 μL/well of 0.5% Triton X-100 in $H_2O$ to release fluorescence. Fluorescence intensity was detected using an Envision® plate reader (Perkin Elmer). For active antagonists in the assay, data were fitted to a 4 parameter logistic equation for $IC_{50}$ determinations.

The potency ($pIC_{50}$) for Example 1 in the cell Adhesion Assays was for: $\alpha_v\beta_6$ $pIC_{50}$=8.0; $\alpha_v\beta_3$ $pIC_{50}$=6.9; $\alpha_v\beta_5$ $pIC_{50}$=7.1; $\alpha_v\beta_8$ $pIC_{50}$=7.6; $\alpha_v\beta_1$ $pIC_{50}$=7.0.

The potency ($pIC_{50}$) for Example 2 in the cell Adhesion Assays was for: $\alpha_v\beta_6$ $pIC_{50}$=7.9; $\alpha_v\beta_3$ $pIC_{50}$=6.2; $\alpha_v\beta_5$ $pIC_{50}$=6.8; $\alpha_v\beta_8$ $pIC_{50}$=7.6.

The potency ($pIC_{50}$) for Example 3 in the cell Adhesion Assays was for: $\alpha_v\beta_6$ $pIC_{50}$=8.2; $\alpha_v\beta_3$ $pIC_{50}$=6.9; $\alpha_v\beta_8$ $pIC_{50}$=7.6; $\alpha_v\beta_1$ $pIC_{50}$=7.1.

The potency ($pIC_{50}$) for Example 4 in the cell Adhesion Assays was for: $\alpha_v\beta_6$ $pIC_{50}$=8.1; $\alpha_v\beta_3$ $pIC_{50}$=6.8; $\alpha_v\beta_8$ $pIC_{50}$=7.6; $\alpha_v\beta_1$ $pIC_{50}$=7.0.

The potency ($pIC_{50}$) for Example 5 in the cell Adhesion Assays was for: $\alpha_v\beta_6$ $pIC_{50}$=7.8; $\alpha_v\beta_3$ $pIC_{50}$=6.1; $\alpha_v\beta_5$ $pIC_{50}$=6.5; $\alpha_v\beta_8$ $pIC_{50}$=7.6; $\alpha_v\beta_1$ $pIC_{50}$=6.8.

The affinity ($pIC_{50}$) for Example 7 in the cell Adhesion Assays was for: $\alpha_v\beta_6$ $pIC_{50}$=6.3; $\alpha_v\beta_3$ $pIC_{50}$=5.5; $\alpha_v\beta_5$ $pIC_{50}$=6.0; $\alpha_v\beta_8$ $pIC_{50}$=5.9.

The affinity ($pIC_{50}$) for Example 8 in the cell Adhesion Assays was for: $\alpha_v\beta_6$ $pIC_{50}$=6.5; $\alpha_v\beta_3$ $pIC_{50}$<5.0.

The affinity ($pIC_{50}$) for Example 9 in the cell Adhesion Assays was for: $\alpha_v\beta_6$ $pIC_{50}$=7.6; $\alpha_v\beta_3$ $pIC_{50}$=5.1; $\alpha_v\beta_5$ $pIC_{50}$=6.5; $\alpha_v\beta_8$ $IC_{50}$=7.1.

Figures quoted are Mean $pIC_{50}$ values.

Permeability in MDCK Cells

The passive membrane permeability of Example 1, Example 2 and Example 5 (all as zwitterion) was determined, in Madin-Darby Canine Kidney-multidrug resistance 1 (MDCKII-MDR1) cells, at pH 7.4 in the presence of the potent P-glycoprotein inhibitor GF120918. Each compound was incubated in duplicate at a concentration of 3-M on each test occasion. In this assay the passive apparent permeability ($P_{app}$) of Example 1 was 68 nm/s (n=2 test occasions) and for Example 2 was 20 nm/s (n=1 test occasion). For Example 5 $P_{app}$ was 90 nm/s (±26 nm/s; n=3 test occasions).

It was observed that although the two diastereoisomeric Examples 1 and Example 2, had similar affinity in vitro in the $\alpha_v\beta_6$ cell adhesion assay (Example 1 $pIC_{50}$=8.0; Example 2 $pIC_{50}$=7.9) they had different permeability in MDCK cells (Example 1 P=68 nm/s and Example 2 P=20 nm/s). This is expected to be reflected by Example 1 having a higher oral availability than Example 2 in vivo in pharmacokinetic studies.

Identification of the Absolute Configuration of Compounds of Structural Formula (I)

Identification of the Absolute Configuration of the 3-Fluoropyrrolidine Asymmetric Centre.

The synthesis of the target molecules (IA) commenced separately with each enantiomer of intermediate of structural formula (IX). This material was purchased from Wuxi App Tec as either the (+)-benzyl 3-fluoro-3-(hydroxymethyl) pyrrolidine-1-carboxylate or the (−)-benzyl 3-fluoro-3-(hydroxymethyl)pyrrolidine-1-carboxylate and each one provided a major diastereoisomer of (IA) which was more potent than the minor diastereoisomer. The absolute configuration of each of the enantiomers of benzyl 3-fluoro-3-(hydroxymethyl) pyrrolidine-1-carboxylate (IX) was not known, and the following experiments outlined in scheme 3 were undertaken to establish their configuration.

A racemic mixture of 1-(tert-butoxycarbonyl)-3-fluoropyrrolidine-3-carboxylic acid (XVII) [Chemical Abstracts registry number 1001754-59-1] (available from Wuxi App Tec) was converted to the N-α-methylbenzylamide by reaction of the acid (XVII) with first carbonyl diimidazole (CDI), followed by (+)-(R)-α-methylbenzylamine. This provided a diastereoisomeric mixture of amides, separable by chromatography on silica gel (P. K. Mykhailiuk et. al. Convenient synthesis of enantiopure (R)- and (S)-3-fluoro-3-aminomethylpyrrolidines, *Tetrahedron* 2014, 70, 3011-3017). The configuration of the more polar isomer was established independently by both Mykhailiuk and us by X-ray diffraction studies and shown to be (S)-tert-butyl 3-fluoro-3-(((R)-1-phenylethyl)carbamoyl)pyrrolidine-1-carboxylate [compound (XVIII)] (FIG. 1), and hence for the less polar isomer as (R)-tert-butyl 3-fluoro-3-(((R)-1-phenylethyl)carbamoyl) pyrrolidine-1-carboxylate [compound (XIX)]. Furthermore this provided reference materials for comparison with the compound obtained by the sequence shown in Scheme III. Although our X-ray data on the polar isomer [compound (XVIII)] was in agreement with the X-ray crystal structure reported by Mykhailiuk et. al. the $^1$H NMR spectrum differed from the spectrum we obtained. The spectra for the two diastereoisomers [compounds (XVIII) and (XIX)] were very similar; however, there was a small diagnostic difference for the pyrrolidine C4 proton. We observe it at 2.22 ppm. Mykhailiuk reported it to be at 2.15 ppm.

The (−)-enantiomer of compound of structural formula (IX) [(−)-benzyl 3-fluoro-3-(hydroxymethyl)pyrrolidine-1-carboxylate], which provided the diastereoisomer of (IA) Example 2 was hydrogenated over 10% Pd/C in ethanol to remove the CBZ protecting group, and the resulting amine (XX) protected with di-tert-butyl dicarbonate to give (−)-tert-butyl 3-fluoro-3-(hydroxymethyl)pyrrolidine-1-carboxylate (XXI). The latter was oxidised with ruthenium trichloride and sodium periodate in acetonitrile-water. The resulting carboxylic acid (XXII) was then converted to the amide as before using CDI and (+)-(R)-α-methylbenzylamine. This amide was compared with the reference amide samples (XVIII) and (XIX) and it was found to be identical by NMR spectroscopy, optical rotation and chiral HPLC to (R)-tert-butyl 3-fluoro-3-(((R)-1-phenylethyl) carbamoyl)pyrrolidine-1-carboxylate (XIX). The (−)-enantiomer of (IX) is the isomer providing the diastereoisomers (IA3) and (IA4) and these have the (R)-configuration at the pyrrolidine asymmetric centre. The (+)-enantiomer of (IX) provided (IA1) and (IA2) which have the absolute configuration (S) at the pyrrolidine asymmetric centre.

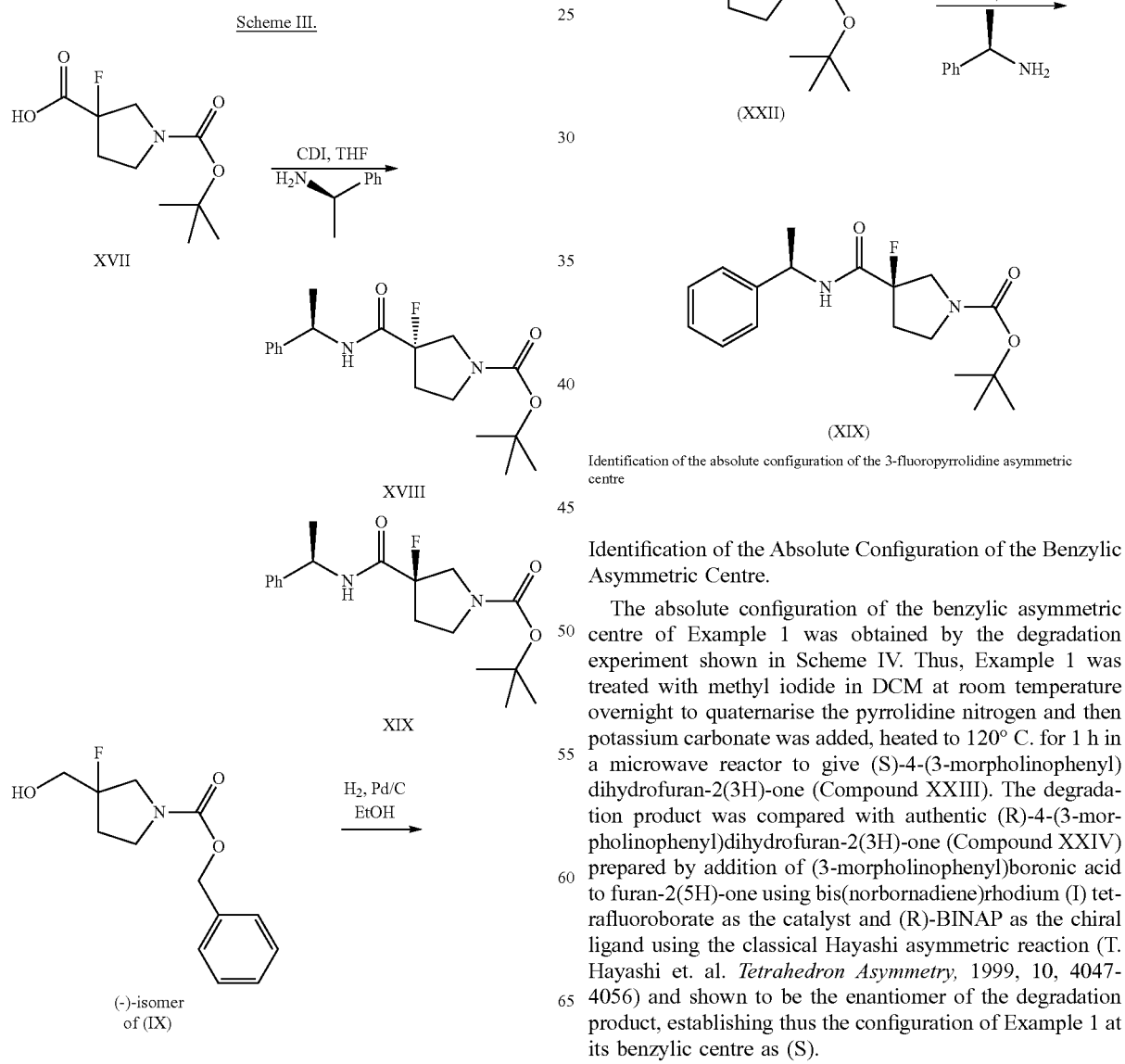

Identification of the absolute configuration of the 3-fluoropyrrolidine asymmetric centre Identification of the Absolute Configuration of the Benzylic Asymmetric Centre.

The absolute configuration of the benzylic asymmetric centre of Example 1 was obtained by the degradation experiment shown in Scheme IV. Thus, Example 1 was treated with methyl iodide in DCM at room temperature overnight to quaternarise the pyrrolidine nitrogen and then potassium carbonate was added, heated to 120° C. for 1 h in a microwave reactor to give (S)-4-(3-morpholinophenyl)dihydrofuran-2(3H)-one (Compound XXIII). The degradation product was compared with authentic (R)-4-(3-morpholinophenyl)dihydrofuran-2(3H)-one (Compound XXIV) prepared by addition of (3-morpholinophenyl)boronic acid to furan-2(5H)-one using bis(norbornadiene)rhodium (I) tetrafluoroborate as the catalyst and (R)-BINAP as the chiral ligand using the classical Hayashi asymmetric reaction (T. Hayashi et. al. *Tetrahedron Asymmetry*, 1999, 10, 4047-4056) and shown to be the enantiomer of the degradation product, establishing thus the configuration of Example 1 at its benzylic centre as (S).

Scheme IV.

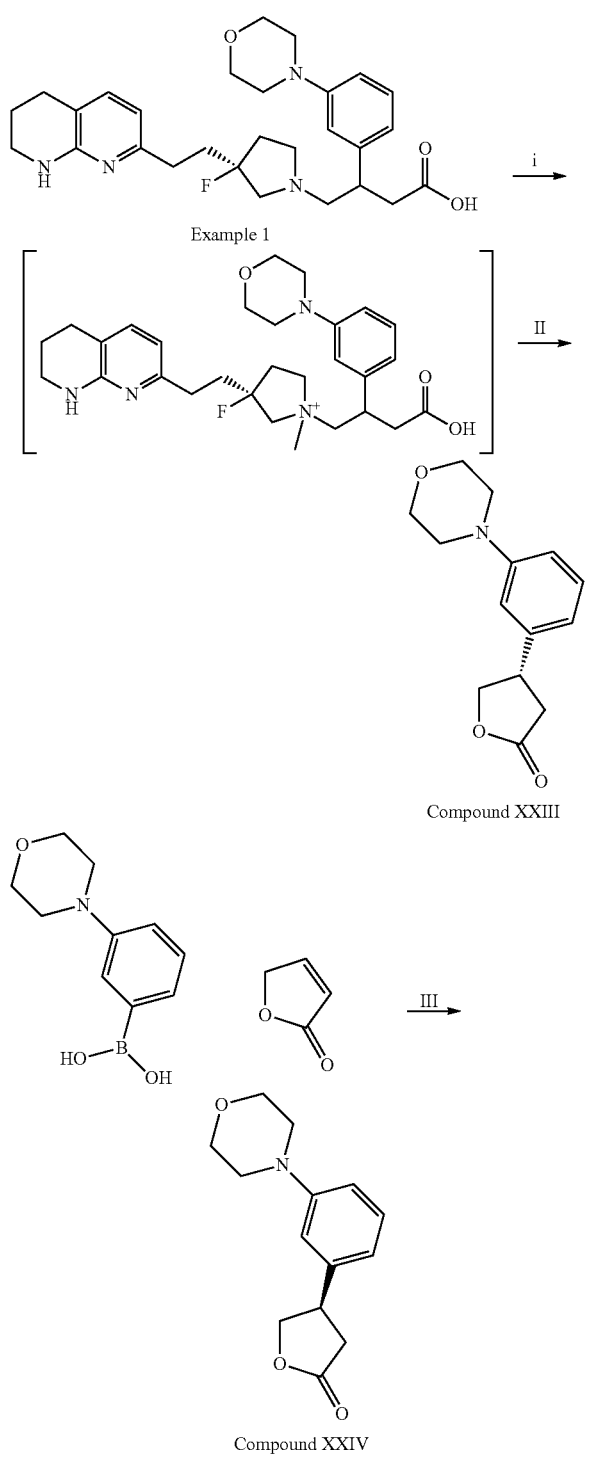

Example 1

Compound XXIII

Compound XXIV

Reagents and conditions: i) MeI, DCM, room temperature, 18 h; ii) K$_2$CO$_3$, 120° C., 1 h; iii) bis(norbornadiene)rhodium (I) tetrafluoroborate and (R)-BINAP, KOH, 1,4-dioxane, 100° C., 1 h.

Furthermore the configuration of compound XXIII was independently confirmed by an X-ray diffraction study and shown to be (S) (FIG. 2).

Based on the above experiments to identify the absolute configuration of each asymmetric centre in compound of structural formula (I) the absolute configuration of the Examples is summarised as follows:

Example 1 is compound of structural formula (IA2) (S)-4-((S)-3-fluoro-3-(2-(5, 6, 7, 8-tetrahydro-1, 8-naphthyridin-2-yl) ethyl) pyrrolidin-1-yl)-3-(3-morpholinophenyl) butanoic acid Example 2 is compound of structural formula (IA3) (S)-4-(R)-(3-fluoro-3-(2-(5, 6, 7, 8-tetrahydro-1, 8-naphthyridin-2-yl) ethyl) pyrrolidin-1-yl)-3-(3-morpholinophenyl) butanoic acid.

EXPERIMENTAL

(S)-tert-butyl 3-fluoro-3-(((R)-1-phenylethylcarbamoyl)pyrrolidine-1-carboxylate (Compound XVIII) and (R)-tert-Butyl 3-fluoro-3-(((R)-1-phenylethyl)carbamoyl)pyrrolidine-1-carboxylate (Compound XIX)

A solution of (±)-1-(tert-butoxycarbonyl)-3-fluoropyrrolidine-3-carboxylic acid (compound XVII) [Chemical Abstracts registry number 1001754-59-1] (available from Wuxi App Tec) (3.00 g, 12.9 mmol) in THF (70 mL) was treated at room temperature with solid CDI (2.5 g, 15.4 mmol) and then the mixture was heated to 80° C. for 1.5 h. (R)-(+)-α-methylbenzylamine (available from Fluka) (1.6 g, 13.2 mmol) was added at this temperature and then the mixture was heated for a further 1.5 h at 80° C. The mixture was diluted with ethyl acetate and washed with dilute HCl, NaHCO$_3$, brine, dried (MgSO$_4$), filtered and allowed to evaporate slowly at room temperature. The mixture was finally concentrated under reduced pressure as no solid crystallised out. The residue was purified by chromatography on silica (2×100 g) cartridges eluting with 0-25% EtOAc-cyclohexane over 40 min. The compound eluting first was obtained as a white foam (1.54 g, 36%): LCMS (System A) RT=1.17 min, ES+ve m/z 337 (M+H)$^+$; $^1$H NMR (500 MHz, CDCl$_3$) 1.43-1.49 (m, 9H), 1.54 (d, J=7.0 Hz, 3H), 2.08-2.19 (m, 1H), 2.37-2.62 (m, 1H), 3.43-3.56 (m, 1H), 3.61-3.93 (m, 3H), 5.14 (quin, J=7.1 Hz, 1H), 6.71-6.76 (m, 1H), 7.27-7.39 (m, 5H) contains about 10% of the more polar diastereoisomer; $[\alpha]_D^{20}$+61 (c=1.27 in MeOH); Analytical Chiral HPLC RT=7.58 min, 90%, and RT=9.53 min, 10% on a Chiralpak AD column (250 mm×4.6 mm), eluting with 10% EtOH-heptane, flow rate=1 mL/min, detecting at 215 nm. A 50 mg portion of this sample was further purified on a silica cartridge (20 g) eluting with 0-25% EtOAc-cyclohexane over 20 min. The appropriate fraction was evaporated under reduced pressure to give an analytically pure sample (30 mg) of (R)-tert-Butyl 3-fluoro-3-(((R)-1-phenylethyl)carbamoyl)pyrrolidine-1-carboxylate (compound XIX) LCMS (System C) RT=1.16 min, ES+ve m/z 337 (M+H)$^+$ and 354 (M+NH$_4$)$^+$ and ES-ve m/z 335 (M−H)$^-$; $[\alpha]_D^{20}$+63 (c=0.933 in MeOH).

The second compound eluting from the column (more polar diastereoisomer) (1.2 g, 28%) was crystallised from ether to give white crystals of (S)-tert-butyl 3-fluoro-3-(((R)-1-phenylethyl)carbamoyl)pyrrolidine-1-carboxylate (compound XVIII): mp=113-115° C.; LCMS (System C) RT=1.16 min, ES+ve m/z 337 (M+H)$^+$; $^1$H NMR (500 MHz, CDCl$_3$) 1.43-1.48 (m, 9H), 1.54 (d, J=7.0 Hz, 3H), 2.14-2.26 (m, 1H), 2.44-2.70 (m, 1H), 3.46-3.55 (m, 1H), 3.56-3.87 (m, 3H), 5.14 (quin, J=7.1 Hz, 1H), 6.73 (br s, 1H), 7.27-7.40 (m, 5H); $[\alpha]_D^{20}$+73 (c=0.876 in MeOH); Analytical Chiral HPLC RT=9.50 min, 100% on a Chiralpak AD column (250 mm×4.6 mm) eluting with 10% EtOH-heptane, flow rate=1 mL/min, detecting at 215 nm. The absolute configuration of this diastereoisomer was established from an X-ray diffraction study.

(R)-(−)-(3-Fluoropyrrolidin-3-yl)methanol (Compound XX)

A solution of (−)-N—CBZ-3-fluoro-3-(hydroxymethyl) pyrrolidine, (−)-isomer of compound (IX), (available from Wuxi App Tec) (4.0 g, 15.8 mmol) was hydrogenated over 10% Pd/C (400 mg) in ethanol (150 mL) overnight. The catalyst was removed by filtration through celite and washed with ethanol. The filtrate and washings were evaporated under reduced pressure to give the title compound (2.0 g, 106%, contains some ethanol by NMR) as a yellow oil, which solidified into a waxy solid: LCMS (System C) RT=0.22 min, ES+ve m/z 120 (M+H)+ and ES-ve m/z 118 (M−H)−. The product was further dried in a blow-down unit under nitrogen at 40° C. $^1$H NMR (500 MHz, CDCl$_3$) 3.82 (dd, J=18.7, 12.5 Hz, 1H), 3.73 (dd, J=22.0, 12.2 Hz, 1H), 3.22-3.15 (m, 1H), 3.23-3.14 (m, 1H), 2.99-2.92 (m, 1H), 2.91 (dd, J=29.1, 13.2 Hz, 1H), 2.66 (br s, 2H), 2.10-1.98 (m, 1H), 1.94-1.81 (m, 1H); $[\alpha]_D^{20}$=−4 (c=1.19 in EtOH).

(R)-(−)-tert-Butyl 3-fluoro-3-(hydroxymethyl)pyrrolidine-1-carboxylate (Compound XXI)

A solution of (R)-(3-fluoropyrrolidin-3-yl)methanol (compound XX) (1.88 g, 15.8 mmol) in DCM (15 mL) and diisopropylethylamine (4.13 mL, 23.7 mmol) was treated with di-tert-butyl dicarbonate (3.79 g, 17 mmol) and the mixture was stirred at 20° C. for 3 h. The mixture was partitioned between 2M HCl and DCM and separated in a phase separator cartridge. The organic layer was concentrated under reduced pressure and the residue was purified by chromatography on a silica cartridge (70 g) eluting with a gradient of 0-50% EtOAc-cyclohexane over 40 min. The fractions were checked by TLC on silica (50% EtOAc-cyclohexane) and stained with KMnO$_4$ solution. Appropriate fractions were combined and evaporated under reduced pressure to give the title compound (2.73 g, 79%) as a colourless oil: LCMS (System C) RT=0.79 min, ES+ve m/z 220 (M+H)+ and 439 (2M+H)+; $^1$H NMR (400 MHz, DMSO-d$_6$) δ 1.42 (s, 9H), 1.96-2.14 (m, 2H), 3.32-3.41 (m, 2H), 3.42-3.50 (m, 2H), 3.54-3.61 (m, 1H), 3.62-3.69 (m, 1H), 4.90 (t, J=5.8 Hz, 1H); $[\alpha]_D^{20}$=−28 (c=3.51 in CHCl$_3$).

(R)-tert-Butyl 3-fluoro-3-(((R)-1-phenylethyl) carbamoyl) pyrrolidine-1-carboxylate (Compound XIX)

A solution of (−)-tert-butyl 3-fluoro-3-(hydroxymethyl) pyrrolidine-1-carboxylate (compound XXI) (200 mg, 0.9 mmol) in MeCN (1 mL) and water (1 mL) was treated with RuCl$_3$ (9.5 mg, 0.05 mmol) and sodium periodate (976 mg, 4.5 mmol) and the mixture was stirred at 20° C. for 16 h. The mixture was acidified with 1M HCl (5 mL) and partitioned in DCM. The aqueous phase was re-extracted twice with DCM and the phases separated in a phase-separation cartridge. The organic solution was evaporated in a blow-down unit to give (R)-1-(tert-butoxycarbonyl)-3-fluoropyrrolidine-3-carboxylic acid (compound XXII) (125 mg, 59%): MS ES-ve m/z 232 (M−H)−. The acid (125 mg, 0.54 mmol) was dissolved in ethyl acetate (10 mL) and treated with CDI (360 mg, 2.2 mmol) and the mixture was stirred at room temperature for 1 h and then heated at 50° C. for 0.5 h. The mixture was concentrated in a blow-down unit, the residue was dissolved in THF (6 mL) and treated with (R)-(+)-α-methylbenzylamine (200 mg, 1.9 mmol) and stirred at 20° C. for 1.5 h. The mixture was diluted with ethyl acetate and washed with 2M HCl solution twice, followed by brine. The organic solution was dried (MgSO$_4$) and evaporated under reduced pressure to give a grey solid (290 mg). The residue was dissolved in MeOH-DMSO (1:1; 3 mL) and purified by MDAP on a XSELECT CSH C18 column (150 mm×30 mm i.d. 5 μm packing diameter) at ambient temperature, eluting with a gradient of 30-85% (10 mM ammonium bicarbonate in water adjusted to pH 10 with aq. ammonia solution—acetonitrile) running for 30 min, detecting at 254 nm and collecting the peak with RT=17.4 min, ES+ve m/z 337 (M+H)+. The fraction was concentrated in a blow-down unit at 45° C. under nitrogen and the residual suspension was extracted with EtOAc. The organic solution was washed with 2 M HCl twice and then with brine, dried (MgSO$_4$) and evaporated under reduced pressure to give a yellow gum (35 mg). The gum was re-purified by MDAP on a XBridge C18 column (100 mm×19 mm i.d. 5 μm packing diameter) at ambient temperature eluting with a gradient of (10 mM ammonium bicarbonate in water adjusted to pH 10 with aq. ammonia solution—acetonitrile) running for 25 min, detecting at 254 nm) collecting the first fraction (RT=10 min). The solvent was removed in a blow-down unit under nitrogen at 45° C. to give the title compound (16 mg, 5%) as a colourless gum: LCMS (System C) RT=1.16 min, ES+ve m/z 337 (M+H)+, 354 (M+NH$_4$)+; Analytical Chiral HPLC RT=7.58 min, 97.7% on a Chiralpak AD column (250 mm×4.6 mm) eluting with 10% EtOH-heptane, flow rate=1 mL/min, detecting at 215 nm; $[\alpha]_D^{20}$+63 (c=1.15 in MeOH). The $^1$H NMR spectrum (500 MHz, CDCl$_3$) as well as the optical rotation and the chiral HPLC RT all match those of (R)-tert-butyl 3-fluoro-3-(((R)-1-phenylethyl)carbamoyl) pyrrolidine-1-carboxylate (compound XIX).

Determination of the Absolute Configuration of the Benzylic Asymmetric Centre of Example 1 by Degradation to (+)-(S)-4-(3-morpholinophenyl)dihydrofuran-2(3H)-one (Compound XXIII)

A solution of (S)-4-((S)-3-fluoro-3-(2-(5,6,7,8-tetrahydro-1,8-naphthyridin-2-yl)ethyl)pyrrolidin-1-yl)-3-(3-morpholinophenyl)butanoic acid_(Example 1)_(100 mg, 0.201 mmol) in DCM (8 mL) at room temperature was treated with iodomethane (0.195 mL, 3.13 mmol) and stirred for 18 h. The reaction was concentrated in vacuo (to remove excess iodomethane). The residue was re-dissolved in DCM (5 mL) and was added potassium carbonate (122 mg, 0.884 mmol). The reaction was heated in a microwave reactor to 120° C. for 1 h. The solution was filtered and concentrated in vacuo. The residual oil was purified by column chromatography on silica (10 g) eluting with a gradient of 0-100% TBME in cyclohexane. The relevant fractions were concentrated in vacuo to give (S)-4-(3-morpholinophenyl)dihydrofuran-2(3h)-one (compound XXIII) (32 mg, 64%) as a white solid: LCMS (System C) RT=0.82 min, 100%, ES+ve m/z 247 (M+H)+; $^1$H NMR (400 MHz, CDCl$_3$) 7.32-7.26 (m, 1H), 6.89-6.84 (m, 1H), 6.79-6.73 (m, 2H), 4.67 (dd, J=9, 8 Hz, 1H), 4.30 (dd, J=9.06, 7.5 Hz, 1H), 3.92-3.85 (m, 4H), 3.76 (quin, J=8.31 Hz, 1H), 3.21-3.17 (m, 4H), 2.93 (dd, J=17.5, 8.7 Hz, 1H), 2.93 (dd, J=17.5, 8.7 Hz, 1H), 2.70 (dd, J=17.5, 8.7 Hz, 1H); $[\bullet]_D^{22}$=+37.1 (c=1.40 in CHCl$_3$); Chiral HPLC RT=25.4 min on a Chiralpak ID column (25 cm×4.6 mm) eluting with 20% isopropanol-heptane, flow-rate 1 mL/min, detecting at 215 nm. A portion of compound XXIII was recrystallised from chloroform by slow crystallisation to provide crystals which were suitable for an X-ray diffraction study.

Synthesis of Authentic (R)-4-(3-morpholinophenyl) dihydrofuran-2(3H)-one (Compound XXIV) for Comparison with Compound (XXIII)

A solution of bis(norbornadiene)rhodium (I) tetrafluoroborate (available from Aldrich) (18.70 mg, 0.05 mmol) and (3-morpholinophenyl)boronic acid (1035 mg, 5.00 mmol) in 1,4-dioxane (10 mL) was treated with furan-2(5H)-one (0.142 mL, 2.0 mmol) and KOH solution (3.8 M, 1.053 mL, 4.00 mmol). The resulting solution was heated to 100° C. for 1 h in a microwave reactor. The reaction was allowed to cool and concentrated in vacuo to give a brown oil. The residue was purified by chromatography (50 g KPNH cartridge) eluting with a gradient of 0-50% EtOAc in cyclohexane over 45 min. The relevant fractions were concentrated in vacuo to give (R)-4-(3-morpholinophenyl)dihydrofuran-2(3H)-one (compound XXIV) (132 mg, 27%) as a white solid: LCMS (System C) RT=0.82 min, 100%, ES+ve m/z 248 (M+H)$^+$; $[\bullet]_D^{22}$=−28.3 (C=1.70 in CHCl$_3$); Chiral HPLC RT=23.4 min, 94%, RT=25.4 min 6% on a Chiralpak ID column (25 cm×4.6 mm) eluting with 20% isopropanol-heptane, flow-rate 1 mL/min, detecting at 215 nm.

The invention claimed is:
1. A compound of formula (I):

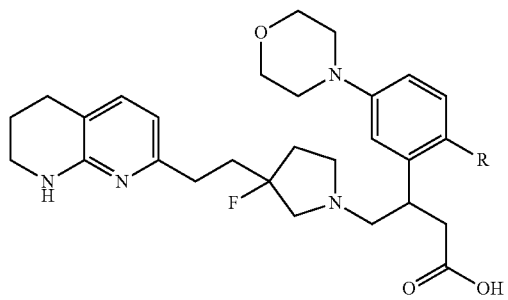

(I)

wherein R is H or F;
or a pharmaceutically acceptable salt thereof.
2. The compound according to claim 1 which is 4-(3-fluoro-3-(2-(5,6,7,8-tetrahydro-1,8-naphthyridin-2-yl)ethyl)pyrrolidin-1-yl)-3-(3-morpholinophenyl)butanoic acid

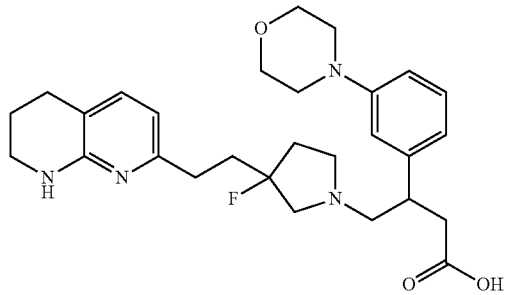 [SMILES: O=C(O)CC(CN1CCC(F)(CCc2ccc3c(n2)NCCC3)C1)c1cccc(N2CCOCC2)c1]

or a pharmaceutically acceptable salt thereof.
3. The compound according to claim 2 which is (S)-4-((S)-3-fluoro-3-(2-(5,6,7,8-tetrahydro-1,8-naphthyridin-2-yl)ethyl)pyrrolidin-1-yl)-3-(3-morpholinophenyl)butanoic acid

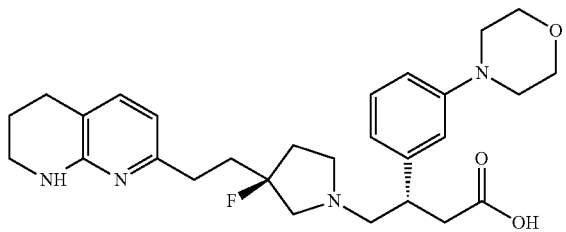 [SMILES: O=C(O)C[C@H](CN1CC[C@@](F)(CCc2ccc3c(n2)NCCC3)C1)c1cccc(N2CCOCC2)c1]

or a pharmaceutically acceptable salt thereof.
4. The compound according to claim 1 which is 4-(3-fluoro-3-(2-(5,6,7,8-tetrahydro-1,8-naphthyridin-2-yl)ethyl)pyrrolidin-1-yl)-3-(2-fluoro-5-morpholinophenyl)butanoic acid

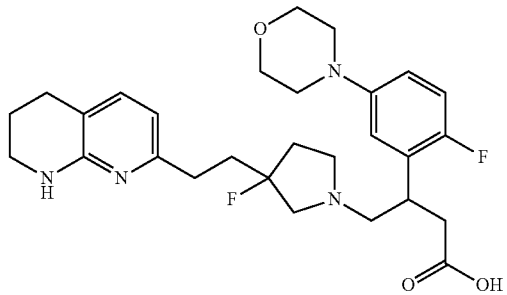 [SMILES: O=C(O)CC(CN1CCC(F)(CCc2ccc3c(n2)NCCC3)C1)c1cc(N2CCOCC2)ccc1F]

or a pharmaceutically acceptable salt thereof.
5. The compound according to claim 4 which is (S)-4-((S)-3-fluoro-3-(2-(5,6,7,8-tetrahydro-1,8-naphthyridin-2-yl)ethyl)pyrrolidin-1-yl)-3-(2-fluoro-5-morpholinophenyl)butanoic acid

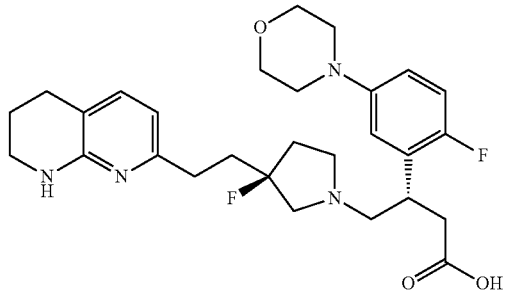 [SMILES: O=C(O)C[C@H](CN1CC[C@@](F)(CCc2ccc3c(n2)NCCC3)C1)c1cc(N2CCOCC2)ccc1F]

or a pharmaceutically acceptable salt thereof.
6. A method of treating a disorder in a human, wherein the disorder is responsive to antagonism of an $\alpha_v\beta_6$ receptor and is a fibrotic disease or condition, the method comprising administering to the human in need thereof a therapeutically effective amount of the compound or pharmaceutically acceptable salt according to claim 1.
7. A method of treating a disorder in a human, wherein the disorder is responsive to antagonism of an $\alpha_v\beta_6$ receptor and is a fibrotic disease or condition, the method comprising administering to the human in need thereof a therapeutically effective amount of the compound or pharmaceutically acceptable salt according to claim 3.

8. A method of treating a disorder in a human, wherein the disorder is responsive to antagonism of an $\alpha_v\beta_6$ receptor and is a fibrotic disease or condition, the method comprising administering to the human in need thereof a therapeutically effective amount of the compound or pharmaceutically acceptable salt according to claim 5.

9. The method according to claim 6, wherein the disorder is idiopathic pulmonary fibrosis.

10. The method according to claim 7, wherein the disorder is idiopathic pulmonary fibrosis.

11. The method according to claim 8, wherein the disorder is idiopathic pulmonary fibrosis.

12. A pharmaceutical composition comprising the compound or pharmaceutically acceptable salt according to claim 1, and a pharmaceutically acceptable excipient.

13. A pharmaceutical composition comprising the compound or pharmaceutically acceptable salt according to claim 3, and a pharmaceutically acceptable excipient.

14. A pharmaceutical composition comprising the compound or pharmaceutically acceptable salt according to claim 5, and a pharmaceutically acceptable excipient.

15. The pharmaceutical composition according to claim 12, wherein the pharmaceutical composition is for oral administration.

16. The pharmaceutical composition according to claim 13, wherein the pharmaceutical composition is for oral administration.

17. The pharmaceutical composition according to claim 14, wherein the pharmaceutical composition is for oral administration.

* * * * *